United States Patent [19]

Lowe, III

[11] Patent Number: 5,641,786
[45] Date of Patent: Jun. 24, 1997

[54] QUINUCLIDINE DERIVATIVES

[76] Inventor: John Adams Lowe, III, 235 E. 42nd St., New York, N.Y. 10017

[21] Appl. No.: 403,987

[22] Filed: Mar. 14, 1995

Related U.S. Application Data

[60] Division of Ser. No. 988,125, Feb. 1, 1993, Pat. No. 5,422,354, which is a continuation-in-part of Ser. No. 557,442, Jul. 23, 1990, abandoned.

[51] Int. Cl.$^6$ ............ A61K 31/44; C07D 453/00; C07D 453/02; C07D 221/22
[52] U.S. Cl. ............... 514/294; 546/79; 546/93; 546/94
[58] Field of Search ............... 546/93, 79, 94; 514/294

[56] References Cited

U.S. PATENT DOCUMENTS

| | | | |
|---|---|---|---|
| 2,455,949 | 6/1948 | Rieveschl, Jr., et al. | 260/570 |
| 4,097,528 | 6/1978 | Porta et al. | 260/570 R |
| 4,246,201 | 1/1981 | Borzatta | 564/317 |
| 5,422,354 | 6/1995 | Lowe | 514/294 |

*Primary Examiner*—Alan L. Rotman
*Attorney, Agent, or Firm*—Peter C. Richardson; Paul H. Ginsburg; Grover F. Fuller, Jr.

[57] ABSTRACT

Quinuclidine derivatives of the formula

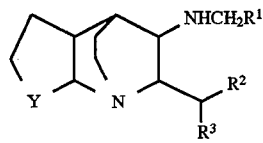

I

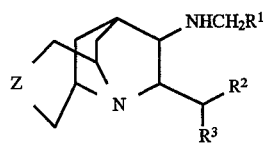

II or

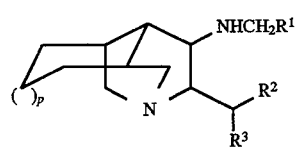

III and the pharmaceutically acceptable salts thereof, wherein m, P, Z, Y, $R^1$, $R^2$ and $R^3$ are as defined below. The compounds are substance P antagonist and, therefore, are useful in treating gastrointestinal disorders, central nervous system disorders, inflammatory diseases, pain and migraine.

17 Claims, No Drawings

QUINUCLIDINE DERIVATIVES

This is a division, of application Ser. No. 07/988,125, filed on Feb. 1, 1993, U.S. Pat. No. 5,422,354 which is the U.S. National Phase of international application No. PCT/US91/03369 filed May 14, 1991, which is a continuation-in-part of U.S. Ser. No. 07/557,442 filed Jul. 23, 1990, now abandoned.

BACKGROUND OF THE INVENTION

This invention relates to quinuclidine derivatives. The compounds of the invention have the ability to antagonize substance P. The compounds are, therefore, useful in treating conditions such as intestinal disorders, central nervous system disorders, inflammatory diseases, pain and migraine. The present invention also relates to pharmaceutical compositions comprising such compounds and to the use of such compounds in treating the foregoing conditions.

E. J. Warawa in U.S. Pat. No. 3,560,510 refers to certain 3-amino-2-benzhydrylquinuclidines as being useful as diuretic agents, with the corresponding unsubstituted 3-benzylamino compounds acting as intermediates for same. Additionally, E. J. Warawa et al. in the *Journal of Medicinal Chemistry*, Vol. 18, p. 587 (1975) extends this work to other members of the series wherein the 3-amino moiety is either ethylamino, beta-phenylethylamino, beta-isopropyl-amino or 2-furfurylamino, but in no instance is there any substitution on the phenyl group itself and the 2-benzhydryl moiety is always symmetrically substituted (or unsubstituted). Neither of the aforementioned documents teaches or suggests any of these compounds to be useful as substance P antagonists.

PCT patent application PCT/US 89/05338, filed Nov. 20, 1989 and assigned in common with the present application, refers to cis-3-[(cyclic)methylamino]-2-[(alpha-substituted) arylmethyl]quinuclidines, 3-[(cyclic)methylimino]-2-[(alpha-substituted)arylmethyl]quinuclidines and cis-3-[(cyclic)methyleneamino]-2-[alpha-substituted)arylmethyl] quinuclidines and states that they are useful as substance P antagonists. U.S. patent application Ser. No. 619,361, filed Nov. 28, 1990 and assigned in common with the present application, refers to carbotricyclic ring systems wherein one of the rings is substituted with an amino group and wherein one carbon atom in each of two of the rings may be replaced by a hetero atom, and states that they are useful as substance P antagonists. (KD-cite PC 7797A).

Substance P is a naturally occurring undecapeptide belonging to the tachykinin family of peptides, the latter being so-named because of their prompt stimulatory action on smooth muscle tissue. More specifically, substance P is a pharmacologically-active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine [see B. E. B. Sandberg et al., *Journal of Medicinal Chemistry*, Vol. 25, p. 1009 (1982)], as well as in central nervous system disorders such as anxiety and schizophrenia, in respiratory and inflammatory diseases such as asthma and rheumatoid arthritis, respectively, and in gastrointestinal disorders and diseases of the GI tract, like ulcerative colitis and Crohn's disease, etc. (see D. Regoli in "Trends in Cluster Headache," Edited by F. Sicuteri et al., Elsevier Scientific Publishers, Amsterdam, 1987, pp. 85–95).

SUMMARY OF THE INVENTION

The present invention relates to compounds of the formula

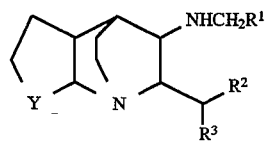   I

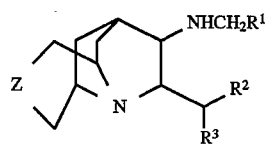   II or

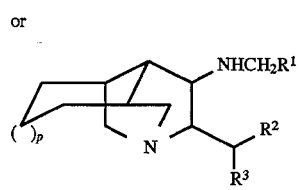   III wherein Y is $(CH_2)_m$ wherein m is an integer from one to three, or Y is a group of the formula

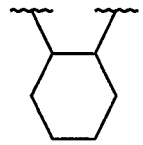   (J)

(hereinafter referred to as a group of the formula J);

p is an integer from zero to one;

Z is oxygen, sulfur, amino, N—$(C_1$–$C_3)$alkylamino or $(CH_2)_n$ wherein n is zero, one or two;

$R^1$ is cycloalkyl having from five to seven carbon atoms, pyrrolyl, thienyl, pyridyl, phenyl, or substituted phenyl, wherein said substituted phenyl is substituted with one to three substituents selected from fluorine, chlorine, bromine, trifluromethyl, alkyl having from one to three carbon atoms, alkoxy having from one to three carbon atoms, carboxy, alkoxycarbonyl having from one to three carbons in the alkoxy moiety and benzyloxycarbonyl;

$R^2$ is furyl, thienyl, pyridyl, indolyl, biphenyl, phenyl, or substituted phenyl, wherein said substituted phenyl is substituted with one or two substituents selected from fluorine, chlorine, bromine, trifluromethyl, alkyl having from one to three carbon atoms, alkoxy having from one to three carbon atoms, carboxy, alkoxycarbonyl having from one to three carbon atoms in the alkoxy moiety and benzyloxycarbonyl; and $R^3$ is thienyl, phenyl, fluorophenyl, chlorophenyl or bromophenyl;

and the pharmaceutically acceptable salts of such compounds.

Compounds of the formula I wherein Y is a group of the formula J are depicted below.

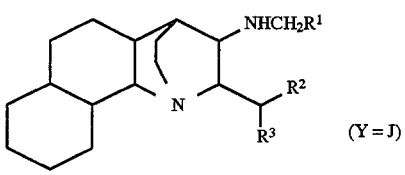

(I)

(Y = J)

Preferred compounds of the present invention are compounds of the formula II. More preferred compounds of the present invention are compounds of the formula II wherein each of $R^2$ and $R^3$ are selected from phenyl and p-fluorophenyl, $R^1$ is selected from 2-methoxyphenyl, phenyl and 2-chlorophenyl, and Z is oxygen or $(CH_2)_n$ wherein n is zero or one.

Specific preferred compounds of the present invention are:

cis-8-(diphenylmethyl)-N-((2-chlorophenyl)methyl))-9-azatricyclo[4.3.1.0$^{4,9}$]decan-7-amine;

cis-8-(diphenylmethyl)-N-((2-methoxyphenyl)methyl))-9-azatricyclo[4.3.1.0$^{4,9}$]decan-7-amine; and cis-9-(diphenylmethyl)-N-((2-methoxyphenyl)methyl-10-azatricyclo[4.4.1.0$^{5,10}$]undecane-8-amine.

Other compounds of the present invention are:

9-(diphenylmethyl)-N-((2-methoxyphenyl)methyl)-3-thia-10-azatricyclo[4.4.1.0$^{5,10}$]undecan-8-amine;

9-(diphenylmethyl)-N-((2-chlorophenyl)methyl)-3-thia-10-azatricyclo[4.4.1.0$^{5,10}$]undecan-8-amine;

3-methyl-9-(diphenylmethyl)-N-((2-methoxyphenyl)methyl)-3,10-diazatricyclo[4.4.1.0$^{5,10}$]undecan-8-amine;

3-methyl-9-(diphenylmethyl)-N-((2-chlorophenyl)methyl)-3,10-diazatricyclo [4.4.1.0$^{5,10}$]undecan-8-amine;

3-acetyl-9-(diphenylmethyl)-N-((2-methoxypheny1)methyl)-3,10-diazatricyclo [4.4.1.0$^{5,10}$]undecan-8-amine;

3-acetyl-9-(diphenylmethyl)-N-((2-chlorophenyl)methyl)-3,10-diazatricyclo [4.4.1.0$^{5,10}$]undecan-8-amine;

8-(diphenylmethyl)-N-((5-fluoro,2-methoxyphenyl)methyl)-9-azatricyclo[4.3.1.0$^{4,9}$]decan-7-amine;

8-(diphenylmethyl)-N-((5-chloro,2-methoxyphenyl)methyl)-9-azatricyclo [4.3.1.0$^{4,9}$]decan-7-amine;

5,6-pentamethylene-3-((5-fluoro,2-methoxy)methylamino)-2-benzhydrylquinuclidine;

5,6-pentamethylene-3-((5-chloro,2-methoxy)methylamino)-2-benzhydrylquinuclidine;

5,6-trimethylene-3-((5-fluoro,2-methoxy)methylamino)-2-benzhydrylquinuclidine;

5,6-trimethylene-3-((5-chloro,2-methoxy)methylamino)-2-benzhydrylquinuclidine;

9-(bis(4-fluorophenyl)methyl))-N-((2-methoxyphenyl)methyl)-10-azatricyclo [4.4.1.0$^{5,10}$]undecan-8-amine;

9-(bis(4-fluorophenyl)methyl))-N-((5-fluoro,2-methoxyphenyl)methyl)-10-azatricyclo [4.4.1.0$^{5,10}$]undecan-8-amine;

2-(diphenylmethyl)dodecahydro-N-(2-methoxyphenyl)methyl)-2H-1,4-methanobenzo[h]quinolin-3-amine;

cis-8-(diphenylmethyl)-N-(phenylmethyl)-7-azatricyclo [4.4.1.0$^{5,10}$]undecan-9-amine;

cis-8-(diphenylmethyl)-N-((2-methoxyphenyl)methyl)-7-azatricyclo[4.4.1.0$^{5,10}$]undecan-9-amine;

cis-8-(diphenylmethyl)-N-((2-chlorophenyl)methyl)-7-azatricyclo[4.4.1.0$^{5,10}$]undecan-9-amine;

cis-8-(diphenylmethyl)-N-((2-trifluoromethylphenyl)methyl)-7-azatricyclo[4.4.1.0$^{5,10}$]undecan-9-amine;

cis-8-diphenylmethyl-N-((2-methoxyphenyl)methyl)-7-azatricyclo[4.3.1.0$^{4,9}$]decan-9-amine;

8-(bis(4-fluorophenyl)methyl))-N-((2-chlorophenyl)methyl)-9-azatricyclo[4.3.1.0$^{4,9}$]decan-7-amine; and 5,6-pentamethylene-3-((2-methoxy)methylamino)-2-(bis(4-fluorophenyl)methyl))quinuclidine.

The compounds of formula I, formula II and formula III may contain chiral centers and therefore may exist in different isomeric forms. This invention includes all geometric isomers and stereoisomers of compounds of the formulae I, II and III, including mixtures thereof.

This invention also includes all radiolabelled forms of the compounds of the formulae I, II and III. Such radio-labelled compounds are useful as research and diagnostic tools in metabolism pharmacokinetic studies and in binding assays in both animal and man. Specific applications in research include radioligand binding assays, autoradiography studies and in vivo binding studies, while specific applications in the diagnostic area include studies of the substance P receptor in the human brain, such as up/down regulation in a disease state, and in vivo binding in the relevant tissues for inflammation, e.g., immune-type cells or cells that are directly involved in inflammatory bowel disorders and the like.

The present invention also relates to a pharmaceutical composition useful for treating a condition selected from gastrointestinal disorders, central nervous system disorders, inflammatory diseases, pain and migraine in a mammal (e.g., a human) in need of such treatment, comprising an amount of a compound having either formula I, formula II or formula III, or a pharmaceutically acceptable salt thereof, effective in antagonizing the effects of substance P at its receptor site, and a pharmaceutically acceptable carrier.

The present invention also relates to a method of treating a condition selected from gastrointestinal disorders, central nervous system disorders, inflammatory diseases, pain and migraine in a mammal in need of such treatment, comprising administering to said mammal an amount of a compound having either having formula I, formula II or formula III, or a pharmaceutically acceptable salt thereof, effective in antagonizing the effects of substance P at its receptor site.

The present invention also relates to a method for antagonizing the effects of substance P at its receptor site in a mammal, comprising administering to such mammal an amount of a compound having either formula I, formula II or formula III, or a pharmaceutically acceptable salt thereof, effective in antagonizing the effects of substance P at its receptor site.

DETAILED DESCRIPTION OF THE INVENTION

Compounds of the formulae I, II and III may be prepared as shown in reaction schemes 1-3 and described below.

Except where otherwise indicated, in the reaction schemes and discussion that follow, $R^1$, $R^2$, $R^3$, Y, Z, m, n and p are defined as above.

SCHEME 1

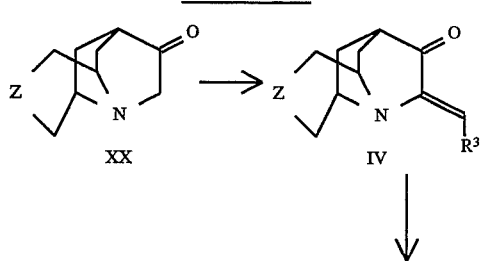

-continued
SCHEME 1
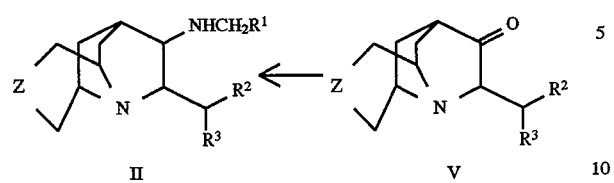
SCHEME 2
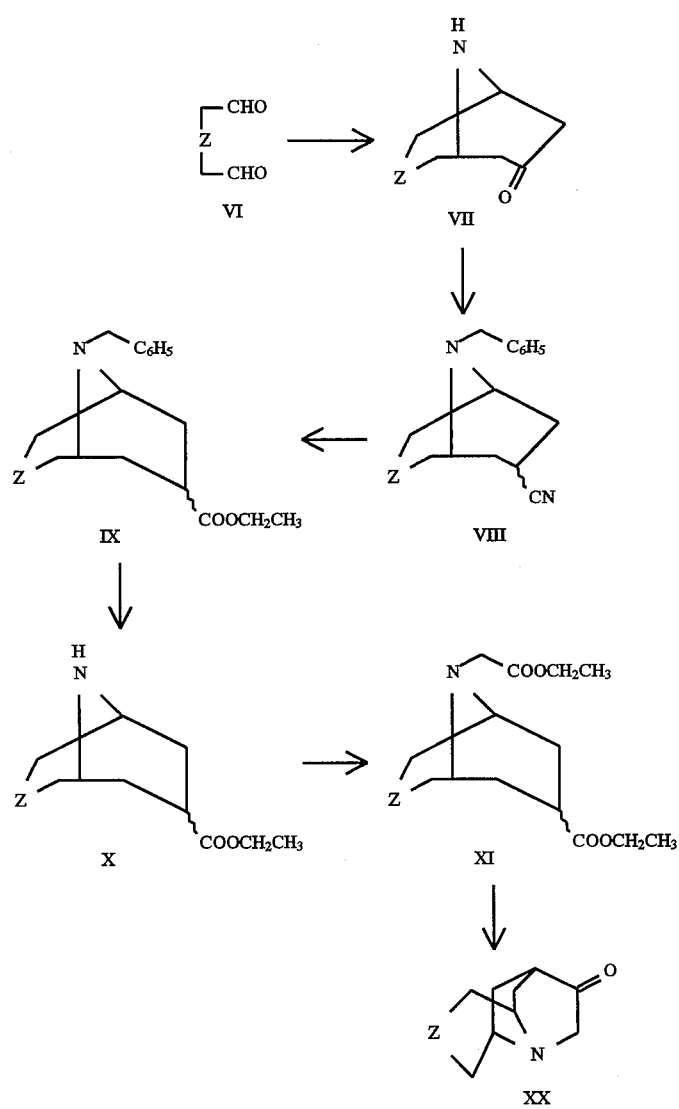

SCHEME 3

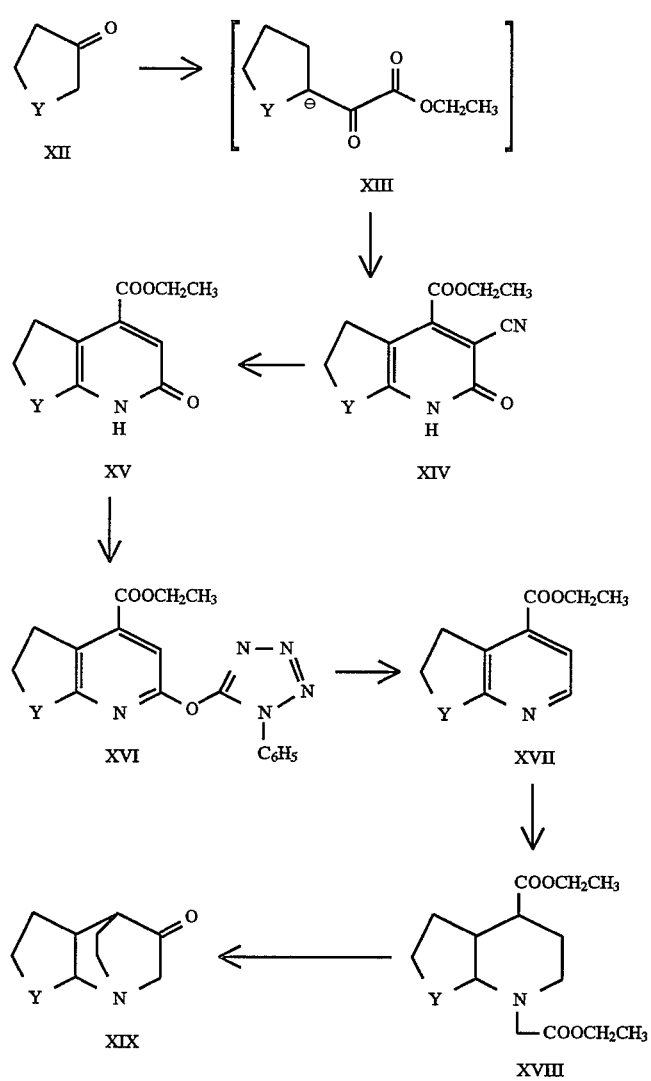

Scheme 1 illustrates a method for preparing compounds of the formula II.

The starting materials used in the procedure of scheme 1, i.e. compounds of the formula XX, may be prepared from known compounds according to the procedure depicted in Scheme 2 and described below. However, those compounds of the formula XX wherein Z is $(CH_2)_n$ and n is zero are known in the art and may also be prepared as described by Schneider et al., Arch. Pharm., 309, 447 (1976).

Referring to Scheme 1, a compound of the formula XX is treated with a compound of the formula $R^3CHO$. This reaction is typically carried out in a reaction inert aqueous or organic solvent. Suitable solvents include water, lower alcohols, ether, tetrahydrofuran (THF), dimethylformamide (DMF), benzene, toluene, hexane, methylene chloride and chloroform. Ethanol is the preferred solvent. Preferably, the reaction is run in the presence of a basic catalyst. Sodium hydroxide is the preferred catalyst, but other bases such as alkali and alkaline earth metal hydroxides, carbonates and alkoxides, as well as organic amine bases such as trialkylamines and pyridine may also be used. Generally, the reaction is run for about 10 minutes to about 24 hours. The reaction temperature may range from about 0° C. to about 200° C., and is preferably about the reflux temperature of the solvent.

The above reaction yields a compound of the formula IV, which is then reacted with a compound of the formula $R^2MgX$, wherein X is chloro, fluoro, bromo or iodo, to form a compound of the formula V. This reaction is usually carried out in a reaction inert hydrocarbon, chlorohydrocarbon or ethereal solvent such as benzene, ether, toluene, hexane, THF or ethyl acetate. The preferred solvent is ether. The reaction is usually run for about 1 minute to about 10 hours. Suitable reaction temperatures range from about −70° C. to about 100° C., with about 0° C. being preferred. The compound of formula V so formed is then converted to the corresponding desired compound of formula II by reacting it with a compound of the formula $R^1CH_2NH_2$, and then treating the reaction mixture with a reducing agent.

The reaction of the compound of formula V with $R^1CH_2NH_2$ is typically carried out in a reaction inert hydrocarbon or chlorohydrocarbon solvent, in the presence of an acidic catalyst. Examples of solvents that may be used include hexane, benzene, toluene, chloroform, methylene chloride, ether, THF, and ethyl acetate. Examples of catalysts that may be used include mineral acids, titanium trichloride, molecular sieves and organic acids such as camphor sulfonic acid. Toluene is the preferred solvent and camphor sulfonic acid is the preferred catalyst. This reaction is generally conducted over a period of about 0.5 hours to about 24 hours, at a temperature from about room temperature to about 220° C. Preferably, the reaction temperature is about 110° C.

The reaction mixture is then treated with a reducing agent, as indicated above, to obtain the desired compound of formula II. Reducing agents that may be used include 9-borobicyclononane (9-BBN), triethylsilane and metal hydrides such as sodium borohydride and sodium triacetoxyborohydride. The preferred reducing agent is 9-BBN. Generally, the reduction is carried out in a reaction inert hydrocarbon, chlorohydrocarbon, carboxyhydrocarbon, aqueous or alcoholic solvent. Water, lower alcohols, trifluoroacetic acid, benzene, toluene, ether, hexane, THF, ethyl acetate and chloroform are suitable, with THF being preferred when the reducing agent is 9BBN. The preferred reaction temperature is about room temperature, but the reduction may be carried out at temperatures ranging from about room temperature to about 200° C.

Scheme 2 illustrates the synthesis of compounds of the formula XX, the starting materials used in the procedure of Scheme 1. Referring to Scheme 2, a compound of the formula VI is reacted with 1,3 acetonedicarboxylic acid and benzylamine in a reaction inert solvent such as water. The Ph is adjusted to about 5, e.g. by the addition of a mineral acid, and maintained at about that value for about 0.5 to about 24 hours. The reaction is generally conducted at a temperature from about room temperature to about the reflux temperature of the solvent, preferably at about room temperature. This reaction produces a compound of the formula VII, which is then reacted with tosylmethyisocyanide in the presence of a lower alcohol such as ethanol and an alkali metal alkoxide such as potassium t-butoxide, at a temperature from about 0° C. to about the reflux temperature of the solvent, preferably at about 50° C. This reaction produces a compound of the formula VIII. Suitable solvents for this reaction include dimethylsulfoxide (DMSO), dimethylformamide (DMF), ether, THF and glyme.

The compound of the formula VIII is then reacted with a lower alcohol saturated with hydrogen chloride gas. Typically, the reaction mixture is heated to reflux, water is added to the mixture, and refluxing is continued for a period of about 0.5 to about 24 hours. This reaction may be conducted to a temperature ranging from about room temperature to about the reflux temperature of the solvent, with the reflux temperature being preferred. The product of the reaction, a compound of the formula IX, is then reduced to form a compound of the formula X using ammonium formate in the presence of a noble metal catalyst such as palladium in a reaction inert solvent such as a lower alcohol. Preferably, the solvent is ethanol. The reduction may be carried out at a temperature from about room temperature to about the reflux temperature of the solvent, preferably at about the reflux temperature.

The compound of formula X so formed may be converted to a compound having formula XI by reacting it with a halogenated acetic acid ester such as ethylbromoacetate in a reaction inert solvent such as a lower alcohol, acetone, acetonitrile, THF, chloroform, hexane or toluene, at a temperature from about room temperature to about the reflux temperature of the solvent. It is preferable to use ethylbromoacetate in ethanol and conduct the reaction at the reflux temperature.

The compound of formula XI may be converted to the corresponding desired compound of formula III in the following manner. First, it is reacted with an alkali or alkaline earth metal alkoxide, preferably potassium ethoxide, in a reaction inert hydrocarbon solvent such as toluene, benzene or hexane at a temperature from about room temperature to about the reflux temperature of the solvent, preferably at about the reflux temperature. The solvent is then evaporated and the residue taken up in a mineral acid such as dilute hydrochloric or dilute sulfuric acid. An ethereal hydrocarbon solvent, e.g. dioxane, may be added optionally as a co-solvent. This final step is also preferably conducted at the reflux temperature of the solvent, with temperatures from about room temperature to about the reflux temperature being suitable.

Compounds of the formula I may be prepared by a procedure analogous to that depicted in Scheme 1 and described above, with the exception that the starting material, rather than being a compound of the formula XX, as depicted in scheme 1, is a compound of the formula XIX, as depicted in scheme 3.

Scheme 3 illustrates the preparation of compounds of the formula XIX from known compounds. Compounds of the formula XII, the starting materials for the reaction sequence of scheme 3, have the following structure when Y is a group of the formula J:

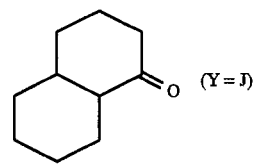

XII

This compound is known in the art and is commercially available (Aldrich®, no. 15, 503–6 (1990)).

Referring to Scheme 3, a compound of the formula XII is reacted with diethyloxylate in a reaction inert solvent such as water or a lower alcohol, preferably ethanol, in the presence of an alkali metal alkoxide or hydroxide, preferably sodium ethoxide, at a temperature from about 0° C. to about the reflux temperature of the solvent, preferably at about 0° C. This reaction forms an intermediate having the formula XIII, which optionally may be isolated by filtration. If isolated by filtration, it is resuspended in the same solvent.

Treatment of the compound of formula XIII with cyanoacetamide at a temperature from about room temperature to about the reflux temperature of the solvent, preferably at about the reflux temperature, yields a compound of the formula XIV. This compound is converted to a compound of the formula XV by the following two steps. First, it is reacted with a strong mineral acid such as hydrochloric acid or sulfuric acid, preferably concentrated hydrochloric acid. Acetic acid may optionally be used as a co-solvent. This reaction is typically carried out at a temperature from about room temperature to about the reflux temperature of the solvent, preferably at about the reflux temperature. After evaporation and filtration, the resulting residue is taken up in thionyl chloride and refluxed for about 0.5 to about 6.9 hours. Excess thionyl chloride is then removed by evaporation in vacuo, and the residue treated with a lower alcohol at a temperature from about 0° C. to about the reflux temperature of the solvent, preferably at about room temperature.

The compound of formula V so formed is reacted with 5-chloro-1-phenyltetrazole in a reaction inert solvent such as acetonitrile, acetone, methylene chloride or a lower alcohol or ethereal solvent, in the presence of a base such as an alkali metal hydroxide or carbonate or an organic base such as a trialkylamine. Generally, this reaction is conducted at a temperature from about room temperature to the reflux temperature of the solvent. The reflux temperature is preferred.

The above reaction yields a compound of the formula XVI. Conversion of this compound to the corresponding compound of formula XVII, as shown in Scheme 3, is accomplished by reacting it with ammonium formate in a lower alcohol in the presence of a palladium catalyst, at a temperature from about room temperature to about the reflux temperature of the solvent, preferably at about the reflux temperature. The compound of formula XVII is then reacted with a halogenated acetic acid ester, e.g. ethyl bromoacetate. This reaction is usually carried out in a reaction inert solvent such as a lower alcohol, acetone, acetonitrile, THF, chloroform, benzene or toluene, at a temperature from about room temperature to about the reflux temperature of the solvent. It is preferable to use ethylbromoacetate in ethanol and to run the reaction at reflux. The reaction mixture is then evaporated and the residue taken up in a solvent such as water or a lower alcohol and treated with a metal hydride reducing agent such as sodium borohydride. The reaction mixture is then concentrated and subjected to hydrogenation. Generally, the hydrogenation is carried out in the presence of a noble metal catalyst such as platinum or palladium, at a hydrogen gas pressure of about 0.5 to about 100 atmospheres. Both of the above reduction steps may be carried out at a temperature from about room temperature to about the reflux temperature of the solvent, preferably at about the reflux being preferred. The metal hydride reduction step may optionally be eliminated. It does, however, result in a higher yield.

The above reactions form a compound of the formula XVIII, which is converted to the corresponding desired compound of formula XIX as follows. The compound of formula XVIII is reacted with an alkali or alkaline earth metal alkoxide, preferably potassium ethoxide. Suitable reaction inert solvents for this reaction include hydrocarbon solvents such as hexane, benzene and toluene. Suitable reaction temperatures range from about room temperature to about the reflux temperature of the solvent. The reflux temperature is preferred. The solvent is then evaporated and the residue taken up in a mineral acid such as dilute hydrochloric or dilute sulfuric acid. An ethereal hydrocarbon solvent such as dioxane may optionally be used as a co-solvent. Preferably, this reaction is conducted at the reflux temperature of the solvent, but temperatures ranging from about room temperature to about the reflux temperature are also suitable.

Compounds of the formula III may be prepared as illustrated and described below:

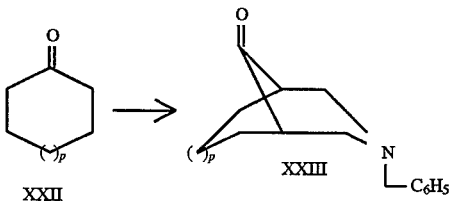

The appropriate cyclic ketone (either cyclopentanone or cyclohexanone) is reacted with benzylamine in the presence of an aqueous solution of formaldehyde and a lower alkanoic acid, preferably acetic acid, at a temperature from room temperature to about the reflux temperature of the solvent, preferably 80° C., for a period from 10 minutes to 24 hours (preferably about 2 hours). After an appropriate workup (adjusting the pH to 8 and extracting the desired product into an organic solvent such as ethyl acetate, a halogenated hydrocarbon, or hydrocarbon), the resulting residue is treated with an alcohol in the presence of an alkanoic anhydride and a strong acid such as a mineral acid, sulfuric acid or phosphoric acid. Preferably, the residue is treated with ethanol in the presence of acetic anhydride and hydrochloric acid. The reaction may be carried out at room temperature to the reflux temperature of the solvent, with room temperature being preferred, and for a period from 10 minutes to 48 hours, with 4 hours being preferred. The hydrochloric acid is preferably added after the reaction has stirred in ethanol and acetic anhydride for 2 hours, after which the reaction is stirred an additional 2 hours.

The foregoing reaction produces a compound of the formula XXIII, as depicted above. This compound may then be converted into a compound of the formula III by the procedure described above for converting compounds of the formula VII into compounds of the formula II, as depicted in schemes 1 and 2 (i.e., reactions VII→VIII→IX→X→XI→XX in scheme 2, followed by reactions XX→IV→V→II in scheme 1).

Unless otherwise indicated, the reaction pressures of the foregoing reactants are not critical, e.g., a reaction pressure of about 0.5 to about 2.0 atmospheres is generally employed, with the preferred pressure usually being at or near ambient pressure (i.e., at about one atmosphere).

Insofar as the majority of the compounds of formulae I, II and III are basic compounds, they are capable of forming a wide variety of different salts with various inorganic and organic acids. Although such salts must be pharmaceutically acceptable for administration to animals, it is often desirable in practice to initially isolate the quinuclidine base compound from the reaction mixture as a pharmaceutically unacceptable salt and then simply convert the latter back to the free base compound by treatment with an alkaline reagent and thereafter, subsequently convert the latter free base to a pharmaceutically acceptable acid addition salt. The acid addition salts of the quinuclidine base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The acids which are used to prepare the pharmaceutically acceptable acid addition salts of the aforementioned quinuclidine base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formulae I, II and III which are also acidic in nature, e.g., where $R^2$ is carboxyphenyl, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formulae I, II and III. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product of yields of the desired final product.

The compounds having formulae I, II and III and their pharmaceutically acceptable salts (hereinafter, also referred to as the active compounds of the present invention) exhibit significant substance P receptor-binding activity and therefore, are of value in the treatment of a wide variety of clinical conditions which are characterized by the excess of said substance P activity. Such conditions include gastrointestinal disorders such as ulcer and colitis and other like diseases of the gastrointestinal tract, central nervous system disorders such as anxiety and psychosis, inflammatory diseases such as rheumatoid arthritis and inflammatory bowel diseases, respiratory diseases such as asthma, as well as pain in any of the aforesaid conditions, including migraine. Hence, these compounds are readily adapted to therapeutic use as substance P antagonists for the control and/or treatment of any of the aforesaid clinical conditions in mammals, including humans. The active compounds of the present invention can be administered via either the oral, parenteral or topical routes. In general, these compounds are most desirably administered in doses ranging from about 5.0 mg up to about 1500 mg per day, although variations will necessarily occur depending upon the weight and condition of the subject being treated and the particular route of administration chosen. However, a dosage level that is in the range of from about 0.07 mg to about 21 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The active compounds of the present invention may be administered alone or in combination with pharmaceutically acceptable carriers by any one of the three routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water ethanol, propylene glycol, glycerin and various like combinations thereof.

For parenteral administration, solutions of an active compound of the present invention in either sesame or peanut oil or in aqueous propylene glycol may be employed. The aqueous solutions should be suitably buffered (preferably Ph greater than 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance P antagonists is determined by their ability to inhibit the binding of substance P at its receptor sites in bovine caudate tissue, employing radioactive ligands to visualize the tachykinin receptors by means of autoradiography. The substance P antagonist activity of the compounds is evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

The anti-inflammatory activity of the compounds of the present invention is demonstrated in the standard carrageenin-induced rat foot edema test [described by C. A. Winter et al., *Proceedings of the Society of Experimental Biology and Medicine*, Vol. 111, p. 544 (1962)]. In this test, anti-inflammatory activity is determined as the percent inhibition of edema formation in the hind paw of male albino rats (weighing 150–190 g) in response to a sub-plantar injection of carrageenin. The carrageenin is injected as a 1% aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving the vehicle alone is significant on comparison with the results afforded by a standard compound like phenylbutazone at 33 mg/kg, via the oral route of administration.

The anti-psychotic activity of the compounds of the present invention as neuroleptic agents for the control of various psychotic disorders is determined by a study of their ability to suppress substance P-induced hypermotility in guinea pigs. This study is carried out by first dosing the guinea pigs with a control compound of with an appropriate test compound of the present invention, then injecting the guinea pigs with substance P by intracerebral ventricular administration via canula and thereafter measuring their individual locomotor response to stimuli.

The following examples illustrate but do not limit the scope of this invention.

EXAMPLE 1

Cis-(1,4-ethano)-3-(phenylmethylamino)-2-benzhydryldecahydroquinoline

A. 1-(Carboethoxymethyl)-4-(carboethoxy)-3-decahydro-quinoline.

To a 1 liter round-bottomed flask equipped with condenser and $N_2$ inlet were added 16.38 g (81.49 mol) ethylguinoline-4-carboxylate, 27.22 g (162.98 mmol) ethyl bromoacetate, and 400 ml ethanol. The solution was heated at reflux for 5 days, cooled, and the solvent evaporated under vacuum. The residue was taken up in 500 ml methanol, and cooled to 0° C. It was then treated with 6.19 g (162.98 mmol) sodium borohydride, and allowed to warm to room temperature. After being stirred for 1 hour at room temperature, the reaction mixture was concentrated, partitioned between methylene chloride and water, the layers separated, and the organic layer washed with water, dried, and evaporated. The residue was chromatographed on silica gel using hexane/ethyl acetate as eluent to afford an oil, 12.13 g (51%), which was reduced directly. The oil was taken up in 200 ml ethanol along with 2.38 ml (41.66 mmol, 1 equivalent) acetic acid and 6 g of 10% palladium on carbon, and reduced with 45 psi hydrogen for four days, adding catalyst and acetic acid to give complete reduction (total 3 ml acetic acid and 10 g catalyst). The catalyst was then filtered off, the solvent evaporated, and the residue partitioned between methylene chloride and water. The organic phase was washed with water, dried and evaporated. The residue was chromatographed on silica gel using ethyl acetate/methylene chloride as eluent to afford 6.99 g (56%) of an oil.

$^1$H NMR ($\delta$, CDCl$_3$): 9.9–2.0 (series of multiplets, 10H), 1.14 (overlapping triplets, 6H), 2.32 (m, 1H), 2.61 (m, 1H), 2.74 (m, 2H), 3.25 (ddd, 2H), 4.0 (overlapping quartets and m, 5H).

$^{13}$C NMR (CDCl$_3$): 14.2, 20.0, 21.5, 22.9, 26.1, 29.5, 39.4, 46.2, 52.9, 53.7, 57.5, 59.8, 59.9, 171.05, 174.0.

MS (%): 297 (parent, 3), 254 (16), 225 (21), 224 (100), 150 (16), 81 (10), 67 (11).

B. (1,4-Ethano)decahydroquinolin-3-one

To a 250 ml three-neck round bottomed flask equipped with condenser and $N_2$ inlet were added 60 ml dry toluene and 2.29 g (58,838 mol) potassium metal. The mixture was heated to reflux, and 2.71 ml (58.838 mmol) ethanol was added slowly. Refluxing was continued until all the potassium had reacted, and then a solution of 6.99 g (23.535 mmol) 1-(carboethoxymethyl)-4-carboethoxydecahydroquinoline in 30 ml toluene was added. The reaction mixture was refluxed for 18 hours, cooled, and the portion soluble in toluene was decanted and evaporated under reduced pressure. The residues were combined and heated in 1N HCl for 24 hours. The reaction mixture was cooled, neutralized with solid sodium bicarbonate, and extracted with methylene chloride. The organic layers were combined, dried, and evaporated to an oil, which was purified by chromatography on silica gel using methanol/methylene chloride as eluent to afford an oil, 1.58 g (37.5%).

$^1$H NMR ($\delta$, CDCl$_3$): 1.1–1.5 (m, 4H), 1.6–1.9 (m, 5H), 1.95 (m, 1H), 2.09 (m, 1H), 2.10 (m, 1H, bridgehead), 2.64 (m, 1H), 2.84 (m, 1H), 3.15 (m, 1H), 3.27 (s, 2H).

MS (%): 180 (parent 1, 23), 179 (parent, 20), 151 (100), 136 (33), 123 (34), 122 (38), 109 (21), 108 (35), 97 (31), 96 (30), 95 (24), 82 (27), 81 (20), 70 (37), 67 (30), 55 (24).

C. (1,4-Ethano)-2-benzylidene-decahydroguinolin-3-one

To a 25 ml round bottomed flask equipped with condenser and $N_2$ inlet were added 1.58 g (8.828 mmol) (1,4-ethano) decahydroquinolin-3-one, 1.404 g (131.242 mmol) benzaldehyde, 4.4 ml ethanol, and 0.071 g (1.765 mmol) sodium hydroxide. The reaction was refluxed for 1 hour cooled, and the resulting yellow crystals collected by filtration, washed with ethanol, and dried to give 1.15 g (49%), mp 69–73C. Additional material was obtained by chromatographing the mother liquor, which was initially washed as a solution in methylene chloride with sodium bisulfite, on silica gel using hexane/ethyl acetate as eluent, to give 848 mg (36%, total 85%).

$^1$H NMR ($\delta$, CDCl$_3$): 1.1–1.9 (m, 9H), 1.9–2.2, m, 2H), 2.35 (m, 1H, bridgehead), 2.6–2.7 (m, 1H), 2.8–3.0 (m, 1H), 3.2–3.3 ((m, 1H), 6.89 (s, 1H), 7.23 (m, 3H), 7.94 (m, 2H).

$^{13}$C NMR (CDCl$_3$): 19.0, 19.1, 19.4, 20.6, 21.8, 34.3, 40.0, 45.4, 56.6, 124.1, 128.4, 129.5, 132.1, 134.1, 146.2, 207.2 (C=O).

IR (cm$^{-1}$, KBr): 1709 (C=O), 1629 (C=C).

MS (%): 268 (parent +1,30), 267 (parent, 95), 239 (100), 238 (82), 170 (45), 157 (94), 156 (43), 148 (39), 130 (40), 117 (44), 116 (34), 91 (31), 67 (42), 55 (37).

D. (1,4-Ethano)-2-benzhydryl-decahydroquinolin-3-one

To a 50 ml round bottomed flask equipped with $N_2$ inlet were added 3.3 ml (10.044 mmol) of a 3M solution of phenyl magnesium bromide in ether and 5 ml dry toluene. The solution was cooled to 0° C., and a solution of 1.7878 g (6.696 mmol) (1,4-ethano)-2-benzylidene-decahydroquinolin-3-one in 10 ml toluene was added dropwise. The reaction mixture was stirred at 0° C. for 1.5 hours, poured into saturated aqueous ammonium chloride, and extracted into methylene chloride. The organic layer was dried and concentrated, and the residue chromatographed on silica gel using hexane/ethyl acetate as eluent to afford 1.47 g (63.6%) of an oil, as a mixture of isomers about the juncture between the cyclohexyl ring and the bicyclic nucleus.

$^1$HNMR ($\delta$, CDCl$_3$): 1.0–2.2 (m, 11H), 2.27 and 2.33 (two multiplets, 1H, bridgehead), 2.4–3.4 (m, 3H), 4.04–4.1 (m, 1H), 4.58 and 4.75 (two doublets, 1H, benzhydryl), 7.1–7.6 (m, 10H).

$^{13}$C NMR (CDCl$_3$): 18.6, 19.2, 19.3, 19.4, 19.6, 20.6, 21.1, 21.7, 22.0, 34.8, 35.5, 36.8, 42.7, 45.9, 46.1, 49.3, 50.9, 51.5, 59.4, 73.7, 74.8, 126.3, 126.5, 127.9, 128.0, 128.2, 128.3, 128.5, 128.8, 128.9, 142.5, 142.6, 143.4, 144.2, 220.0, 220.7.

MS (%): 346 (parent+1, 2.5), 318 (43), 317(96), 274 (36), 180 (71), 167 (31), 165 (37), 150 (100, 84 (43), 49 (34).

E. Cis-(1,4-ethano)-3-(phenylmethylamino)-2-benzhydryldecahydroquinoline

To a 25 ml round bottomed flask equipped with Dean-Stark trap, condenser, and $N_2$ inlet were added 702 mg (2.035 mmol) (1,4-ethano)-2-benzhydryl-decahydroquinolin-3-one, 326.7 mg (3.053 mmol) benzylamine, 20 mg camphorsulfonic acid, and 10 ml toluene. The reaction mixture was refluxed 24 hours, cooled and evaporated. The residue was taken up in 1.3 ml tetrahydrofuran and cooled to 0° C. To the stirring solution was added a 0.5M solution (4.071 mmol) of 9-borabicyclononane in tetrahydrofuran, and the reaction allowed to warm to room temperature and stirred for 3 days. The reaction was poured into a mixture of 1N HCl and methylene chloride, the layers separated, and the aqueous layer adjusted to pH 10 with solid sodium hydroxide. The aqueous layer as then extracted with methylene chloride, and the organic layer dried and evaporated. The residue was crystallized from isopropanol to afford a white solid, 431 mg (49%), mp 125°–145° C., as a mixture of isomers a for the starting material.

$^1$H NMR ($\delta$, CDCl$_3$): 1.2–2.2 (m, 10H), 2.4–3.9 (m, 9H), 4.59 (finely split doublet, 1H, benzhydryl), 6.49 (m, 2H), 7.1–7.6 (m, 13H).

$^{13}$C NMR (CDCl$_3$): 15.4, 19.7, 20.0, 20.2, 20.9, 21.9, 22.0, 22.2, 22.6, 22.7, 28.7, 29.7, 31.1, 35.5, 36.6, 43.7, 49.1, 49.2, 49.7, 52.2, 52.3, 56.1, 56.7, 59.8, 63.8, 64.0, 125.6, 125.8, 126.5, 126.7, 127.9, 128.1, 128.3, 129.3, 139.9, 140.0, 143.1, 143.7, 145.2, 145.3.

MS (%): 437 (parent+1, 1), 345 (13),270 (23), 269 (100).

Anal. Calc'd for $C_{31}H_{36}N_2$: C 85.27, H 8.31, N 6.42. Found: C 84.94, H 8.16, N 6.35.

EXAMPLE 2

Cis-(1,4-ethano)-3-((2-methoxyphenyl)methylamino)-2-benzhydryldecahydroquinoline To a 25 ml round bottomed flask equipped with Dean-Stark trap, condenser, and $N_2$ inlet were added 769 mg (2.229 mmol) (1,4-ethano)-2-benzhydryl-decahydroquinolin-3-one, 458 mg (3.343 mmol) 2-methoxybenzylamine, 20 mg camphorsulfonic acid, and 11 ml toluene. The reaction was refluxed 24 hours, cooled, and evaporated. The residue was taken up in 1.5 ml tetrahydrofuran and cooled to 0° C. To the stirring reaction was added a 0.5M solution (4.458 mmol) of 9-borabicyclononane in tetrahydrofuran, and the reaction allowed to warm to room temperature and stirred 2 days. The reaction was poured into 1N HCl/methylene chloride, the layers separated, and the aqueous layer adjusted to pH 10 with solid sodium hydroxide. The aqueous layer was extracted with methylene chloride, and the organic layer was dried and evaporated. The residue was chromatographed on silica gel using methanol/methylene chloride as eluent to afford an oil, 463 mg (44.5%), again as a mixture of isomers between the cyclohexyl ring and the bicyclic nucleus.

$^1$H NMR ($\delta$, CDCl$_3$): 1.2–2.2 (m, 10H), 2.5–4.0 (m, 9H), 3.52 and 3.56 (two singlets, 3H, OMe), 4.62 (broad doublet, 1H, benzhydryl), 6.6–6.8 (m, 2H), 7.0–7.4 (m, 12H).

$^{13}$C NMR (CDCl$_3$): 14.9, 19.4, 19.7, 19.9, 20.6, 20.8, 22.0, 22.1, 22.2, 28.3, 29.5, 30.8, 35.1, 36.6, 43.6, 46.1, 46.2, 48.7, 49.8, 55.2, 55.3, 55.6, 56.1, 59.9, 63.8, 64.1, 110.0, 120.2, 120.3, 125.9, 126.6, 127.6, 127.7, 127.8, 128.0, 128.2, 128.4, 129.1, 129.2, 129.4, 129.5, 157.4, 157.5.

MS (%): 467 (parent+1, 7), 345 (60), 300 (61), 299 (100), 290 (26), 150 (21), 121 (72), 91 (78).

The oil was dissolved in ether, treated with ether saturated with Hcl gas, and the solid filtered, washed with ether, and dried to afford 340 mg (26.8%), mp 176°–180° C.

Anal. Calc'd for $C_{32}H_{38}N_2O \cdot 2HCl \cdot 2.5H_2O$: C 65.74, H 7.76, N 4.79. Found: C 65.82, H 7.81, N 4.66.

EXAMPLE 3

5,6-Trimethylene-3-((2-methoxyphenyl)methylamino)-2-benzhydryl-quinuclidine

A. 5,6-(Trimethylene)-pyridin-2-one-4-carboxylic acid

To a 250 ml round-bottomed flask equipped with $N_2$ inlet were added 75 ml ethanol followed by 2.37 g (0.10 g-atom) sodium. After reaction was complete, the solution was cooled to 0° C. and there were added 14.98 g (0.101 mol) diethyl oxalate and then 8.42 g (0.10 mol) cyclopentanone dropwise over 10 minutes. The reaction mixture turned to a solid yellow mass within a few minutes, and was swirled by hand intermittently for 25 minutes at 0° C. The bright yellow solid was collected by filtration, then suspended in 100 ml ethanol, to which was added a hot solution of 8.41 g (0.10 mol) cyanoacetamide in 100 ml ethanol. The mixture was refluxed for 3.5 hours, cooled, and the solid filtered and washed with ethanol. The solid was then taken up in water and the pH adjusted to 1.5. The resulting solid was collected (and combined with a second crop from the filtrate), taken up in 250 ml concentrated hydrochloric acid, and refluxed for 12 hours. The resulting mixture was evaporated to near dryness, and the solid collected, washing with a minimal amount of water. The yield of dried product was 7.42 g (41%).

$^1$H NMR ($\delta$, DMSO-d$_6$): 1.97 (m, 2H), 2.71 (t, 2H), 2.86 (t, 2H), 6.60 (s, 1H).

MS (%): 179 (79, parent), 151 (63), 106 (100).

B. Ethyl 5,6-(trimethylene)-pyridin-2-one-4-carboxylate

To a 250 ml round-bottomed flask equipped with reflux condenser and $N_2$ inlet were added 6.42 g 5,6-(trimethylene) pyridin-2-one-4-carboxylic acid and 50 ml thionyl chloride. The mixture was refluxed for 1 hour (giving a solution), and the excess thionyl chloride removed in vacuo. To the residue was added excess ethanol, and after stirring the resulting mixture at room temperature 5 minutes, adding more ethanol, and concentrating, the resulting solid was collected and chromatographed on silica gel using methanol/methylene chloride as eluent to give 7.173 g (83.6%) of a solid.

$^1$H NMR ($\delta$, CDCl$_3$): 1.26 (t, 3H), 2.02 (m, 2H), 2.84 (t, 2H), 2.91 (t, 2H), 4.22 (q, 2H), 6.86 (s, 1H).

IR (cm$^{-1}$, KBr): 1722 and 1654 (C=O).

$^{13}$C NMR (CDCl$_3$): 14.1, 22.5, 20.4, 30.9, 61.5, 118.0, 119.5, 140.5, 152.1, 165.1, 166.1.

MS (%): 207 (69, parent), 178 (100), 106 (37).

Anal. Calc'd for $C_{11}H_{13}NO_3$: C 63.76, H 6.32, N 6.76. Found: C 63.85, H 6.34, N 6.65.

C. Ethyl-5,6-(trimethylene)-2-(1-phenyl-5-tetrazolyloxy)pyridine-4-carboxylate To a 500 ml round-bottomed flask equipped with condenser and $N_2$ inlet were added 6.97 g (33.67 mmol) ethyl-5,6-(trimethylene)-pyridin-2-one-4-carboxylate, 7.30 g (40.41 mmol) 5-chloro-1-phenyl tetrazole, 9.29 g (67.34 mmol) potassium carbonate, and 170 ml acetonitrile. The mixture was refluxed for 18 hours, cooled, and most of the solvent removed in vacuo. The residue was taken up in methylene chloride, washed with water, dried over sodium sulfate, and evaporated. The residue was chromatographed on silica gel using hexane/ethyl acetate as eluent to give an oil which was crystallized from ether/hexane 7.42 g (63%), mp 83–86.

$^1$H NMR ($\delta$, CDCl$_3$): 1.38 (t, 3H), 2.14 (m, 2H), 2.95 (t, 2H), 3.25 (t, 2H), 4.39 (q, 2H), 7.4–7.8 (m, 6H).

IR (cm$^{-1}$, KBr): 1726 (C=O).

$^{13}$C NMR (CDCl$_3$): 14.2, 22.7, 31.1, 33.6, 61.8, 109.6, 109.7, 122.5, 129.7, 132.9, 137.6, 158.2, 159.3, 164.5, 167.5.

MS (%): 351 (7, parent), 323 (100, 295 (33), 178 (50), 132 (38), 118 (47), 117 (79), 77 (50), 65 (57).

Anal. Calc'd for C$_{18}$H$_{17}$N$_5$O$_3$: C 61.53, H 4.88, N 19.93. Found: C 61.50, H 4.68, N 19.71.

D. Ethyl-2,3-trimethylene-pyridine-4-carboxylate

To a 250 ml round-bottomed flask equipped with condenser and N$_2$ inlet were added 12.77 g (36.38mmol) ethyl-5,6-(trimethylene)-2-(1-phenyl-5-tetrazolyloxy)-pyridine-4-carboxylate, 13.75 g (218.3 mmol) ammonium formate, and 182 ml ethanol. Once a solution had been obtained by stirring and heating, 12.77 g (10% palladium on carbon was added, and heating continued to reflux then the mixture was heated for 10 minutes at reflux followed by cooling and filtration through a diatomaceous earth (Celite trademark) pad to remove palladium. The filtrate was evaporated and the residue taken up in methylene chloride and washed with 1N aqueous sodium hydroxide and water, dried over sodium sulfate, and evaporated. The residue was chromatographed on silica gel using hexane/ethyl acetate as eluent to afford an oil, 3.07 g (44%).

$^1$H NMR (δ, CDCl$_3$): 1.24 (t, 3H), 1.96 (m, 2H), 2.89 (t, 2H), 3.12 (t, 2H), 4.22 (q, 2H), 7.37 (d, 1H), 8.26 (d, 1H).

IR (cm$^{-1}$, KBr): 1712 (C=O).

$^{13}$CNMR (CDCl$_3$): 14.2, 22.5, 31.6, 34.0, 61.2, 120.2, 120.3, 121.0, 130.0, 133.6, 137.6, 147.8, 165.8, 167.8.

MS (%): 191 (89, parent), 162 (100), 118 (76), 117 (71), 116 (52), 91 (55), (49).

Exact mass calc'd for C$_{11}$H$_{13}$NO$_2$: 191. 0947. Found: 191.0928.

E. Ethyl-2-ethoxycarbonylmethyl-2-aza-[4.3.0]-bicyclononane

To a 250 ml round-bottomed flask equipped with condenser and N$_2$ inlet were added 3.07 g (16.07 mmol) ethyl 2,3-trimethylene-pyridine-4-carboxylate, 5.37 g (32.15 mmol) ethyl bromoacetate, and 80 ml ethanol. The reaction mixture was refluxed for 4 days, cooled, and most of the solvent evaporated in vacuo. The residue was taken up in 80 ml methanol and treated with 1.22 g ( 32.15 mmol) sodium borohydride at room temperature for 14 hours. The reaction mixture was concentrated, taken up in methylene chloride, washed with water and brine, dried over sodium sulfate, and evaporated. The residue was hydrogenated with platinum oxide under 40 psi hydrogen with 1 ml acetic acid for 2 days, then filtered and concentrated. The residue was chromatographed on silica gel using hexane/ethyl acetate as eluent to afford an oil, 173 g (38%).

$^1$H NMR (δ, CDCl$_3$): 1.18 (m, 6H), 1.3–1.9 (m, 8H), 2.2–2.9 (multiplets, 5H), 3.20 (dd, 2H), 4.07 (m, 4H).

IR (cm$^{-1}$, KBr); 1720 (C=O).

$^{13}$C NMR (CDCl$_3$): 14.1, 21.6, 22.8, 23.0, 30.2, 41.7, 41.9, 52.3, 55.3, 59.89, 59.94, 63.0, 170.9, 174.1.

MS (%): 284 (45, parent+1), 283 (16, parent), 210 (100), 136 (48).

Anal. Calc'd for C$_{15}$H$_{25}$NO$_4$: C 63.58, H 8.89, N 4.94. Found: C 63.43, H 8.94, N 5.29.

F. 5,6-Trimethylene-2-benzylidene-3-quinuclidone

To a 125 ml round-bottomed flask equipped with a condenser and N$_2$ inlet were added 20 ml dry toluene and 0.705 g (18.07 g-atom) potassium. To the refluxing mixture was added 1.06 ml (18.07 mmol) ethanol, and refluxing was continued until reaction was complete. To the refluxing solution was added a solution of 2.05 g (7.23 mmol) ethyl-2-ethoxycarbonylmethyl-2-aza-[4.3.0]-bicyclononane in 20 ml toluene, and refluxing was continued for 14 hours. The reaction mixture was then cooled, the toluene decanted off the brown oil and evaporated, and the organic residues combined in 50 ml 1N HCl and refluxed for 20 hours. The reaction mixture was cooled, neutralized with solid sodium bicarbonate, and extracted with methylene chloride. The organic layer was dried over sodium sulfate and evaporated to an oil. The oil was dissolved in 3 ml ethanol, treated with 1.1 ml (10.84 mmol) benzaldehyde and 60 mg (1.44 mmol) sodium hydroxide, and refluxed for 5 minutes. The reaction mixture was then cooled, taken up in methylene chloride, washed with water, dried over sodium sulfate, and evaporated. The residue was chromatographed on silica gel using hexane/ethyl acetate as eluent to give 1.245 g (68%), mp 85°–95° C.

$^1$H NMR (δ, CDCl$_3$): 1.6–2.8 (series of multiplets, 11H), 3.3–3.5 (m, 2H), 7.02 (s, 1H), 7.3–7.4 (m, 3H), 8.03 (m, 2H).

IR (cm$^{-1}$, KBr): 1690 (C=O). $^{13}$C NMR (CDCl$_3$): 19.2, 26.4, 28.1, 29.4, 37.7, 37.8, 39.7, 44.7, 61.7, 124.1, 128.4, 129.4, 132.1, 134.1, 145.7, 206.9.

MS (%): 253 (100, parent), 224 (52), 157, (55) .

Anal. Calc'd for C$_{17}$H$_{19}$NO: C 80.60, H 7.56, N 5.53. Found: C 80.64, H 7.45, N 5.40.

G. 5,6-Trimethylene-2-benzhydryl-3-quinuclidone

To a 50 ml round-bottomed flask equipped with N$_2$ inlet was added 2.4 ml (7.11 mmol) of a 3.0M solution of phenyl magnesium bromide in ether. The solution was cooled to 0° C., and a solution of 1.2 g (4.74 mmol) of 5,6-trimethylene-2-benzylidene-3-quinuclidone in 10 ml toluene added. The reaction was stirred at room temperature for 10 minutes, poured into saturated aqueous ammonium chloride, and extracted with methylene chloride. The organic layer was dried over sodium sulfate and evaporated to an oil. The oil was chromatographed on silica gel using hexane/ethyl acetate as eluent to afford a mixture of exo and endo products as an oil, 1.054 g (67%).

$^1$H NMR (δ, CDCl$_3$): 1.3–2.6 (m, 8H), 2.8–2.9 (m, 2H), 3.1–3.6 (series of 3 multiplets, 1H each), 4.00 and 4.08 (doublets, 1H, mixture of exo and endo isomers), 4.59 and 4.65 (doublets, 1H, both isomers) 7.1–7.5 9m, 10H).

IR (cm$^{-1}$, KBr): 1715 (C=O).

$^{13}$C NMR (CDCl$_3$): 18.9, 19.4, 26.2, 26.3, 27.7, 28.1, 29.0, 29.2, 34.6, 38.0, 39.3, 42.3, 45.1, 50.1, 51.2, 56.0, 64.7, 72.7, 73.8, 126.3, 126.4, 128.3, 128.4, 142.5, 142.6, 143.3, 143.9, 220.1, 220.6.

MS (%): 303 (41), 180 (28), 136 (100).

Exact mass calc'd for C$_{23}$H$_{26}$NO: 332.2015. Found: 332.2014.

H. 5,6-Trimethylene-3-((2-methoxyphenyl)methylamino]-2-benzhydryl-quinuclidine

To a 50 ml round-bottomed flask equipped with Dean-Stark trap, condenser, and N$_s$ inlet were added 0.996 g (3.01 mmol) 5,6-trimethylene-2-benzhydryl-3-quinuclidone, 0.618 g (4.51mmol) 2-methoxybenzylamine, 3 mg camphorsulfonic acid, and 15 ml toluene. The reaction mixture was refluxed 3 days, cooled, and concentrated. The residue was taken up in 2 ml dry tetrahydrofuran and treated at 0° C. with 12 ml (6.0 mmol) of a 0.5M solution of 9-borabicyclononane in tetrahydrofuran. The reaction mixture was then allowed to warm to room temperature and stirred for 4 days. It was then poured into 1N HCl, washed with methylene chloride and the aqueous layer adjusted to pH 12 and extracted with methylene chloride. The organic layer was dried over sodium sulfate and evaporated to an oil. The oil was chromatographed on silica gel using methanol/methylene chloride as eluent to afford an oil, which was converted to its hydrochloride salt using HCl gas in dry ether to give 773 mg (47%) of a white solid, mp 207°–212° C.

¹H NMR (δ, CDCl₃, free base): 1.2–2.5 (m, 8H), 2.7–3.8 (m, 7H), 3.52 and 3.55 (singlets, 3H, for both exo and endo isomers), 4.6–4.7 (m, 1H), 6.6–6.8 (m, 3H), 7.07–7.4 (m, 10H).

¹³C NMR (CDCl₃, free base): 14.3, 21.0, 25.4, 28.0, 28.1, 28.3, 28.9, 39.0, 30.7, 33.4, 35.8, 37.5, 43.0, 46.1, 46.3, 48.7, 49.3, 53.6, 54.3, 54.9, 55.3, 63.5, 64.5, 110.0, 120.1, 120.2, 125.8, 126.5, 127.7, 127.8, 127.9, 128.0, 128.1, 128.3, 129.1, 129.2, 143.5, 157.4.

MS (%): 453 (1.5, parent+1), 286 (36), 285 (100), 121 (70), 91 (65).

Exact mass calc'd for $C_{31}H_{37}N_2O$: 453. 2906. Found: 453.2903.

Anal. Calc'd for $C_{31}H_{37}N_2O \cdot 2HCl \cdot H_2O$: C 68.50, H 7.42, N 5.15. Found: C 68.59, H 7.80, N 5.08.

EXAMPLE 4

5,6-Trimethylene-3-benzylamino-2-benzhydryl-quinuclidine

The title compound was prepared following the method of Example 3 in 48.9% yield as the hydrochloride salt, mp 185°–189° C.

Anal. Calc'd for $C_{30}H_{34}N_2 \cdot 2HCl \cdot 5/4H_2O$: C 69.55, H 7.49, N 5.41. Found: C 69137, H 7.55, N 5.23.

EXAMPLE 5

8-(Diphenylmethyl)-N-((2-methoxyphenyl)methyl))-9-azatricyclo[4.3.1.0⁴,⁹]decan-7-amine A. 8-Benzylidine-9-azatricyclo[4.3.1.0⁴,⁹]decan-7-one To a 100 ml round-bottomed flask equipped with a condenser and nitrogen inlet were added 1.34 g (8.87 mmol) 9-azatricyclo[4.3.1.0⁴,⁹]decan-7-one (prepared according to the method of W. Schneider, B. Lang, and F. Schumann, Arch. Pharm., 309, 447 (1976)), 0.90 ml (8.87 mmol) benzaldehyde, 30 ml ethanol, and 5 pellets of sodium hydroxide. The mixture was heated at reflux for 2 hr, cooled, and evaporated. The residue was taken up in ethyl acetate, washed with water, saturated aqueous sodium bisulfite solution and brine, dried over sodium sulfate, and evaporated. The resulting yellow oil, 2.07 g (100%), was crystallized from ethanol to give a yellow solid, m.p. 96°–98° C.

¹H-NMR (δ, CDCl₃): 1.6–1.8 (m, 4H), 2.2–2.3 (m, 4H), 2.40 (m, 1H), 3.46 (m, 2H), 7.10 (s, 1H), 7.3–7.4 (m, 2H), 8.0 (m, 2H).

IR (cm⁻¹, neat): 1700, 1615 (C=O, C=C).

MS(%): 239 (58, parent), 211 (72), 210 (100), 117 (43), 116 (43), 84 (49).

Anal. Calc'd for $C_{16}H_{17}NO$: C 80.30, H 7.16, N 5.85. Found: C 80.37, H 7.18, N 5.88.

B. 8-(Diphenylmethyl)-9-azatricyclo[4.3.1.0⁴,⁹]decan-7-one

To a 100 ml three-necked round-bottomed flask equipped with a rubber septum and nitrogen inlet were added 5 ml dry toluene and 4.43 ml (13.3 mmol) of a 3.0M solution of phenyl magnesium bromide in ether. The solution was cooled to 0° C., and a solution of 2.07 g (8.87 mmol) 8-benzylidene-9-azatricyclo[4.3.1.0⁴,⁹]decan-7-one in 20 ml toluene was added over 5 min. The reaction was allowed to stir at 0° C. for 1 hour and then poured into saturated aqueous ammonium chloride. The mixture was extracted into ethyl acetate, and the organic layer washed with saturated aqueous ammonium chloride and brine, dried over sodium sulfate, and evaporated. The residue was chromatographed on silica gel using hexane/ethyl acetate as eluent and the product fractions combined to afford 1.47 g (53%) of a white solid, mp 137°–138° C.

¹H-NMR: (δ, CDCl₃): 1.3–2.4 (multiplets, 10H), 2.23 (m, 1H, bridgehead), 3.54 (m, 1H), 4.11 (d, J=4, 1H), 4.86 (d, J=4, 1H), 7.1–7.3 (m, 8H), 7.5 (m, 2H).

IR (cm⁻¹, CDCl₃): 1712 (C=O).

MS(%) 317 ( 1, parent), 289 (99), 248 (66), 198 (66), 180 (100), 179 (45), 167 (42), 165 (59), 122 (56), 91 (34), 69 (56), 54 (60).

Anal. Calc'd for $C_{22}H_{23}NO$: C 83.24, H 7.30, N 4.41. Found: C 83.40, H 7.41, N 4.42.

C. Cis-8-(diphenylmethyl)-N-((2-methoxyphenyl)methyl)-9-azatricyclo[4.3.1.0⁴,⁹]decan-7-amine To a 100 ml round-bottomed flask equipped with a Dean-Stark trap, condenser, and nitrogen inlet were added 1.47 g (4.71 mmol) 8-(diphenylmethyl)-9-azatricyclo [4.3.1.0⁴,⁹]decan-7-one, 0.92 ml (7.07 mmol) 2-methoxybenzylamine, 2 mg camphorsulfonic acid, and 15 ml toluene. The reaction was refluxed 24 hour, cooled, and the toluene evaporated. To the residue was added 18.8 ml (9.42 mmol) of a 0.5M solution of 9-borabicyclo[3.3.1] nonane in tetrahydrofuran at 0° C., and the reaction allowed to warm to room temperature and stir for 2.5 days. The reaction was evaporated to one-half its original volume, and stirred at room temperature for 2.5 days. The reaction was then evaporated, taken up in a few ml methylene chloride, 50 ml methanol, and 1.5 ml 6N hydrochloric acid, and allowed to stir for 14 hours. The reaction was then evaporated, the residue taken up in ethyl acetate, and the organic layer washed with saturated aqueous sodium bicarbonate solution and brine, dried over sodium sulfate, and evaporated. The residue was chromatographed on silica gel using methanol/methylene chloride as eluent, and the product fractions combined and crystallized from isopropanol to afford 540 mg (26%) of a white solid, mp 116°–117° C.

¹H-NMR (δ, CDCl₃): 1.3–2.0 (series of multiplets, 8H), 2.20 (m, 1H), 2.72 (m, 1H), 3.00 (m, 1H), 3.40 (dd, J=13,96, 2H, benzylic CH2), 3.34 (m, 1H), 3.51 (s, 3H), 3.80 (dd, J=8.2,12, 1H, C-8H, the 8.2 Hz coupling to the adjacent C-7 position is consistent with a cis stereochemical relationship), 4.46 (d, J=12, 1H), 6.5–6.8 (m, 3H), 7.0–7.3 (m, 11H).

IR (cm⁻¹, KBr): 3257 (N—H), 1600 (C=C).

MS(%): 438 (1, parent), 317 (34), 272 (33), 271 (100), 176 (19), 167 (10), 122 (24), 121 (80), 91 (59).

Anal. Calc'd for $C_{30}H_{34}N_2O$: C 82.15, H 7.81, N 6.39. Found: C 82.08, H 7.75, N 6.39.

The title compounds of examples 6–8 were prepared using a procedure analogous to that of Example 5.

EXAMPLE 6

Cis-8-(diphenylmethyl)-N-(phenylmethyl)-9-azatricyclo [4.3.1.0⁴,⁹]decan-7-amine

M.p. 147°–148° C., in 5% yield. ¹H-NMR (δ, CDCl₃): 0.76 (m, 1H), 1.1–2.0 (m, 7H), 2.17 (m, 1H), 2.67 (m, 1H), 2.99 (m, 1H), 3.32 (m, 1H), 3.34 (AB, J=13,112, 2H), 3.81 (dd, J=8.2,12.2, 1H), 4.38 (d, J=12.2, 1H), 6.58 (m, 2H), 7.0–7.4 (m, 13H).

MS(%): 408 (3.6, parent), 407 (5), 318 (17), 317 (70), 242 (18), 241 (100), 91 (34).

Anal. Calc'd for $C_{29}H_{29}N_2$: C 85.25, H 7.89, N 6.86. Found: C 85.12, H 7.77, N 6.80.

EXAMPLE 7

Cis-8-(diphenylmethyl)-N-((2-chlorophenyl) methyl))-9-azatricyclo[4.3.1.0⁴,⁹]decan-7-amine M.p. 159°–160° C., in 12% yield.

¹H-NMR (δ, CDCl₃): 0.76 (m, 1H), 1.1–2.0 (m, 7H), 2.17 (m, 1H), 2.67 (m, 1H), 2.99 (m, 1H), 3.3 (m, 1H), 3.43 (AB, J=13,90, 2H), 3.83 (m, 1H), 4.38 (d, J=12.2, 1H), 6.54 (m, 1H), 7.0–7.4 (13H) .

MS(%): 317 (37), 277 (34), 275 (100), 127 (23), 125 (75).

Anal. Calc'd for $C_{29}H_{31}N_2Cl$: C 78.62, H 7.05, N 6.32. Found: C 78.45, H 7.16, N 6.28.

EXAMPLE 8

Cis-8-(Diphenylmethyl)-N-((4-tri fluoromethylpheny)methyl))-9-azatricyclo[4.3.1.0$^{4,9}$]decan-7-amine M.p. 162°–163.5° C., in 25% yield. $^1$H-NMR ($\delta$, CDCl$_3$): 0.76 (m, 1H), 1.1–2.0 (m, 7H), 2.15 (m, 1H), 2.65 (m, 1H), 3.00 (m, 1H), 3.32 (m, 1H), 3.40 (AB, J=13.5, 108.7, 2H), 3.82 (dd, J=8.2, 12.2, 1H), 4.35 (d, J=12.2, 1H), 6.69 (d, J=8, 2H), 7.0–7.4 (m, 12H).

MS (%): 476 (2, parent), 475 (3.5), 474 (5.5), 318 (16), 317 (65), 310 (19), 309 (100), 159 (21).

Anal. Calc'd for $C_{30}H_{31}N_2F_3$: C 75.61, H 6.56, N 5.88. Found: C 75.38, H 6.55, N 5.87.

EXAMPLE 9

Cis-9-(diphenylmethyl)-N-(phenylmethyl)-10-azatricyclo[4.4.1.0$^{5,10}$]undecane-8-amine A. N-Benzyl-9-azabicyclo[3.3.1]nonan-3-one To a 1 L round-bottomed flask equipped with a condenser and nitrogen inlet were added 80 g (0.2 mol) of a 25% aqueous solution of glutaraldehyde, 29.2 g (0.2 mol) 1,3-acetonedicarboxylic acid, and 11.4 g (0.2 mol) benzylamine. After the initial reaction had subsided, the pH was adjusted to 5 and maintained for 14 hours. The reaction was then taken up in 6N HCl, washed with ethyl acetate, and basified with 6N sodium hydroxide solution. The aqueous layer was extracted with methylene chloride, and the organic layer filtered through diatomaceous earth (Celite [trademark]) and evaporated. The residue was chromatographed on silica gel with ethyl acetate/methylene chloride as eluent to afford 15.034 g (33%) of a pale orange solid, mp 70°–73°0 C.

$^1$H-NMR ($\delta$, CDCl$_3$): 1.48 (m, 4H), 1.90 (m, 2H), 2.20 (m, 2H), 2.68 (m, 2H), 3.26 (m, 2H), 3.86 (s, 2H), 7.1–7.4 (m, 5H).

IR (cm$^{-1}$, KBr): 1690 (C=O).

MS (%): 229 (27, parent).

Anal. Calc'd for $C_{15}H_{19}NO$: C 78.56, H 8.35, N 6.11. Found: C 78.61, H 8.36, N 5.95.

B. N-Benzyl-9-azabicyclo[3.3.1]nonan-3-carbonitrile

To a 500 mL round-bottomed flask equipped with a condenser and nitrogen inlet were added 185 mL dimethoxyethane, 5.00 g (27.62 mmol) N-benzyl-9-azabicyclo[3.3.1]nonan-3-one, and 9.70 g (49.72 mmol) tosylmethylisocyanide. The solution was cooled to 0° C., and 2.92 mL (63.53 mmol) ethanol were added, followed by 10.83 g (96.68 mmol) potassium tert-butoxide in 4 portions. The reaction was then heated at 50° C. for 10 hr, poured into a saturated sodium chloride solution, and extracted into ethyl acetate. The organic layer was filtered through diatomaceous earth (Celite [trademark]) and evaporated. The residue was chromatographed on silica gel with hexane/ethyl acetate as eluent to afford an oil, 1.85 g (35%).

$^1$H-NMR ($\delta$, CDCl$_3$): 1.45 (m, 2H), 1.68 (m, 2H), 1.84 (m, 2H), 2.03 (m, 2H), 2.25 (m, 2H), 2.87 (m, 2H), 3.33 (m, 1H), 3.83 (s, 2H), 7.2–7.4 (m, 5H).

$^{13}$C-NMR (CDCl$_3$): 20.4, 23.6, 26.0, 30.4, 49.3, 56.6, 123.1, 127.0, 128.3, 139.5.

IR (cm$^{-1}$, KBr): 2220 (CN).

MS (%): 240 (77, parent), 172 (50), 91 (100).

High resolution mass spectrum (HRMS), Calc'd for $C_{16}H_{20}N_2$: 240.1622. Found: 240.1628.

C. Ethyl-N-benzyl-9-azabicyclo[3.3.1]nonan-3-carboxylate

To a 125 mL round-bottomed flask equipped with a condenser and nitrogen inlet were added 1.85 g (7.72 mmol) N-benzyl-9-azabicyclo[3.3.1]nonan-3-carbonitrile and 51 mL ethanol. The solution was heated to reflux, 0.9 mL water added, and refluxing continued for 14 hr. The reaction was cooled, concentrated, and partitioned between methylene chloride and a 1N aqueous sodium hydroxide solution. The organic layer was separated, dried over sodium sulfate, and evaporated. The oil was used directly without further purification, yield 80.4%.

$^1$H-NMR ($\delta$, CDCl$_3$): 1.12 (t, J=7, 3H), 1.48 (m, 3H), 1.65 (m, 3H), 1.88 (m, 1H), 2.0–2.2 (m, 4H), 2.92 (m, 1H), 3.12 (m, 1H), 3.85 (s, 2H), 4.10 (q, J=7, 2H), 7.1–7.5 (m, 5H).

MS (%): 287 (24, parent), 229 (25), 214 (54), 186 (45), 173 (42), 172 (65), 170 (21), 92 (20), 91 (100), 65 (22).

D. Ethyl-9-azabicyclo[3.3.1]nonane-3-carboxylate

To a 125 mL round-bottomed flask equipped with a condenser and N$_2$ inlet were added 8.14 g (28.36 mmol) ethyl-N-benzyl-9-azabicyclo[3.3.1]nonane-3-carboxylate, 60 mL ethanol, 8.93 g (141.8 mmol) ammonium formate, and 5 g 10% palladium-on-carbon. The reaction was refluxed and fresh catalyst and ammonium formate were added until the starting material disappeared (about 4 hr, a total of 8 g catalyst). The reaction was cooled, filtered through diatomaceous earth (Celite [trademark]), and evaporated. The residue was partitioned between methylene chloride and an aqueous sodium hydroxide solution, and the organic layer separated, dried over sodium sulfate, and evaporated. The resulting oil was used directly in the next step.

MS (%): 198 (92), 197 (71, parent), 168 (63), 152 (61), 140 (67), 139 (79), 124 (91), 97 (50), 96 (100), 83 (51), 82 (96), 81 (50), 80 (52), 69 (50), 68 (61), 55 (53), 54 (43).

E. Ethyl-N-ethoxycarbonylmethyl-9-azabicyclo[3.3.1]nonane-4-carboxylate

To a 250 mL round-bottomed flask equipped with a condenser and nitrogen inlet were added 5.59 g (28.36 mmol) ethyl-9-azabicyclo[3.3.1]nonane-3-carboxylate, 142 mL ethanol, and 9.47 g (56.72 mmol) ethyl bromoacetate. The reaction was refluxed 3 days, cooled, and evaporated. The residue was partitioned between methylene chloride and aqueous sodium hydroxide, and the organic layer was dried over sodium sulfate and evaporated. The residue was filtered through silica gel using ethyl acetate to afford an oil, 4,835 g (100% yield crude), as a mixture of diastereomers.

$^1$H-NMR ($\delta$, CDCl$_3$): 1.18 (triplets, 6H), 1.2–2.4 (multiplets, 7H), 2.6–3.8 (m, 6H), 3.39, 3.47, 3.75, and 3.98 (singlets, 2H), 4.0–4.2 (quartet, 4H).

MS (%): 283 (15, parent), 21 (49), 210 (100), 182 (36), 168 (30), 152 (71).

F. 9-Benzylidene-10-azatricyclo[4.4.1.0$^{5,10}$]undecan-8-one

To a 250 mL three-necked round-bottomed flask equipped with a condenser and nitrogen inlet were added 45 mL toluene and 1.66 g (42.72 g-atom) potassium. The reaction was heated to reflux, 1.96 mL (42.72 mmol) ethanol added slowly, and refluxing continued until the potassium disappeared. To the refluxing reaction was then added a solution of 4.84 g (17.09 mmol) ethyl-N-ethoxycarbonylmethyl-9-azabicyclo[3.3.1]nonane-3-carboxylate in 20 mL toluene, and the reaction was refluxed 16 hr. The reaction was then cooled and evaporated, and the residue taken up in 85 mL 1N HCl and heated to reflux for 24 hr. The reaction was then cooled, extracted with methylene chloride, and the pH adjusted to 14 with sodium hydroxide. The aqueous layer was extracted with methylene chloride, and the organic layer was dried over sodium sulfate and evaporated. The resultant brown solid (1.34 g, 47.5% yield crude) was taken up in 10 mL ethanol and treated with 1.29 g (12.18 mmol) benzaldehyde and 0.065 g (1.62 mmol) sodium hydroxide. The solution was refluxed 15 min, cooled, and concentrated. The residue was partitioned between water and methylene chloride, and the organic layer separated, dried over sodium sulfate, and evaporated. The residue was chromatographed on silica gel with hexane/ethyl acetate as eluent to afford 1.23 g (60%) of a solid, mp 109°–112° C.

$^1$H-NMR ($\delta$, CDCl$_3$): 1.55 (m, 3H), 1.8–2.2 (multiplets, 7H), 2.54 (m, 1H), 3.18 (m, 2H), 6.96 (s, 1H), 7.32 (m, 3H), 8.07 (m, 2H).

$^{13}$C-NMR (CDCl$_3$): 12.5, 29.6, 30.0, 40.8, 50.2, 124.6, 128.4, 129.5, 132.3, 134.2, 145.1, 207.2.

IR (cm$^{-1}$, KBr): 1700 (C=O), 1625 (C=C).

MS (%): 254 (12), 253 (36, parent), 224 (100), 117 (19), 116 (22), 55 (20).

Anal. Calc'd for Chd $17H_{19}NO$: C 80.60, H 7.56, N 5.53. Found: C 80.64, H 7.64, N 5.48.

G. 9-Benzhydryl-10-azatricyclo[4.4.1.0$^{5,10}$]undecan-8-one

To a 50 mL round-bottomed flask equipped with a nitrogen inlet were added 2.5 mL (7.64 mmol) of a 3M solution of phenyl magnesium bromide in ether and 10 mL toluene. The solution was cooled to 0° C., and a solution of 1.21 g (4.78 mmol) 9-benzylidene-10-azatricyclo[4.4.1.0$^{5,10}$]undecan-8-one in 6 mL toluene was added dropwise. The reaction was stirred at room temperature for 15 min, then poured into saturated aqueous ammonium chloride and extracted with ethyl acetate. The organic layer was dried over sodium sulfate and evaporated. The residue was chromatographed on silica gel with hexane/ethyl acetate as eluent to afford a colorless oil, 1.028 g (65%).

$^1$H-NMR ($\delta$, CDCl$_3$): 1.1–2.1 (multiplets, 10H), 2.37 (m, 1H), 2.75 (m, 1H), 3.23 (m, 1H), 3.77 (d, J=7, 1H), 4.63 (d, J=7, 1H), 7.1–7.5 (m, 10H).

$^{13}$C-NMR (CDCl$_3$): 13.2, 29.0, 29.7, 30.4, 30.8, 41.5, 45.0, 49.7, 53.1, 74.2, 126.2, 126.4, 128.0, 128.4, 128.7, 128.8, 142.6, 143.8.

IR (cm$^{-1}$, KBr): 1702 (C=O).

MS (%): 331 (1, parent), 304 (41), 303 (100), 262 (72), 212 (71), 180 (60), 165 (54), 136 (64), 117 (66), 83 (94), 67 (43).

HRMS, Calc'd for C$_{23}$H$_{25}$NO: 331.2064. Found: 331.2000.

H. Cis-9-(diphenylmethyl)-N-(phenylmethyl)-10-azatricyclo[4.4.1.0$^{5,10}$]undecane-8-amine To a 25 mL round-bottomed flask equipped with a condenser, Dean-Stark trap, and nitrogen inlet were added 514 mg (1.55 mmol) 9-benzhydryl-10-azatricyclo[4.4.1.0$^{5,10}$]undecane-8-one, 10 mL toluene, 249 mg (2.33 mmol) benzylamine, and 2 mg camphorsulfonic acid. The reaction was refluxed for 24 hr, cooled, and the toluene was evaporated. The residue was taken up in 1.2 mL tetrahydrofuran, cooled to 0° C., and treated with 6.22 mL (3.11 mmol) a 0.5M solution of 9-borabicyclo[3.3.1]nonane in tetrahydrofuran. The solution was stirred at room temperature 5 days, partitioned between aqueous HCl and methylene chloride, and the aqueous layer was separated, adjusted to pH 14 with sodium hydroxide and extracted with methylene chloride. The organic layer was dried over sodium sulfate and evaporated. The residue was crystallized from 2-propanol to afford 144 mg (22%) of a white solid, mp 137°–140° C.

$^1$H-NMR ($\delta$, CDCl$_3$): 1.0–1.8 (multiplets, 10H), 2.03 (m, 2H), 2.82 (m, 2H), 3.43 (AB, J=12, 85, 2H), 3.55 (dd, J-9,12 1H), 4.55 (d, J=12, 1H), 6.67 (m, 2H), 7.1–7.4 (13H).

$^{13}$C-NMR (CDCl$_3$): 13.9, 23.3, 25.8, 29.9, 30.1, 30.7, 43.7, 48.8, 52.1, 53.5, 54.2, 65.2, 125.3, 126.5, 126.6, 127.7, 127.8, 128.0, 128.2, 129.2, 140.1, 143.7, 145.5.

MS (%): 421 ( 1, parent-1), 331 (13), 256 (28), 255 (100), 167 (12), 163 (11), 136 (12), 91 (90).

Anal. Calc'd for C$_{30}$H$_{34}$N$_2$: C 85.26, H 8.11, N 6.63. Found: C 84.89, H 8.03, N 6.52.

EXAMPLE 10

Cis-9-(diphenylmethyl)-N-((2-methoxyphenyl)methyl)-10-azatricyclo[4.4.1.0$^{5,10}$]undecane-8-amine The title compound was prepared using a procedure analogous to that of Example 9 in 16% yield as an oil, after purification by chromatography on silica gel with methylene chloride/methanol as eluent.

$^1$H-NMR ($\delta$, CDCl$_3$): 1.0–1.8 (multiplets, 10H), 2.1 (m, 2H), 2.84 (m, 2H), 3.33 (m, 2H), 3.48 (s, 3H), 3.62 (m, 1H), 4.69 (m, 1H), 6.69 (m, 2H), 6.78 (m, 1H), 7.0–7.4 (m, 11H).

$^{13}$C-NMR (CDCl$_3$): 13.7, 23.0, 25.38, 25.42, 29.8, 29.9, 30.5, 43.7, 46.0, 48.6, 53.9, 55.3, 110.0, 120.2, 125.3, 126.5, 127.7, 128.0, 128.2, 128.3, 128.4, 129.1, 129.2, 129.5, 129.59, 129.63, 129.7, 157.5.

MS (%): 452 (1, parent), 331 (21), 286 (29), 285 (100), 167 (11), 165 (14), 136 (13), 122 (12), 121 (84), 91 (63).

The hydrochloride salt was generated with HCl in ether to afford a solid, mp 219°–223° C.

Anal. Calc'd for C$_{31}$H$_{36}$N$_2$O•2HCl•3H$_2$O: C 64.24, H 7.65, N 4.83. Found: C 64.61, H 7.28, N 4.86.

EXAMPLE 11

Cis-9-(diphenylmethyl)-N-((2-methoxyphenyl)methyl)-3-oxa-10-azatricyclo[4.4.1.0$^{5,10}$]undecan-8-amine A. N-Benzyl-7-oxa-9-azabicyclo[3.3.1]nonan-3-one Prepared by a procedure analogous to that of Example 9A in 37% yield, mp 142°–147° C.

$^1$H-NMR ($\delta$, CDCl$_3$): 2.26 (m, 2H), 2.66 (m, 2H), 3.11 (m, 2H), 3.71 (dd, J=12,42, 4H), 3.86 (s, 2H), 7.1–7.4 (m, 5H).

$^{13}$C-NMR (CDCl$_3$): 40.4, 40.5, 55.4, 56.8, 71.9, 127.5, 128.6, 137.9, 207.4.

IR (KBr, cm$^{-1}$): 1695 (C=O).

MS (%): 231 (65, parent), 186 (82), 91 (100), 65 (22).

Anal. Calc'd for C$_{14}$H$_{17}$NO$_2$: C 72.70, H 7.41, N 6.06. Found: C 72.65, H 7.39, N 6.03.

B. N-Benzyl-7-oxa-9-azabicyclo[3.3.1]nonan-3-carbonitrile

Prepared by a procedure analogous to that of Example 9B in 35% yield as an oil.

$^1$H-NMR ($\delta$, CDCl$_3$): 1.87 (m, 2H), 2.24 (m, 2H), 2.63 (broad s, 2H), 3.82 (dd, J=12,48, 4H), 3.84 (s, 2H), 3.9–4.0 (m, 1H), 7.2–7.4 (m, 5H).

$^{13}$C-NMR (CDCl$_3$): 23.4, 27.0, 50.6, 50.7, 55.9, 70.6, 122.8, 127.3, 128.5, 138.2

IR (KBr, cm$^{-1}$): 2165 (CN).

MS (%): 243 (67), 242 (80, parent) 212 (53), 211 (84), 198 (36), 197 (96), 151 (70), 133 (45), 132 (39), 121 (37), 117 (38), 92 (46), 91 (100), 65 (56).

HRMS, Calc'd for C$_{15}$H$_{18}$N$_2$O: 242.1417. Found: 242.1427.

C. Ethyl-N-benzyl-7-oxa-9-azabicyclo[3.3.1]nonan-3-carboxylate

Prepared by a procedure analogous to that of Example 9C in 83% yield as an oil.

$^1$H-NMR ($\delta$, CDCl$_3$): 1.24 (t, J=8, 3H), 1.71 (m, 2H), 2.15 (m, 2H), 2.65 (broad s, 2H), 3.65 (m, 1H), 3.84 (s, 2H), 3.85 (dd, J=12, 42, 4H), 4.13 (g, J=S, 2H), 7.1–7.4 (m, 5H).

$^{13}$C-NMR (CDCl$_3$): 14.3, 25.6, 37.4, 51.5, 55.9, 60.2, 71.3, 127.0, 128.3, 128.5, 138.9, 176.0.

IR (KBr, cm$^{-1}$): 1737 (C=O).

MS (%): 289 (20), 244 (53), 186 (61), 133 (21), 94 (22), 93 (27), 91 (100), 65 (33), 57 (41).

Anal. Calc'd for C$_{17}$H$_{23}$NO$_3$: C 70.56, H 8.01, N 4.84. Found: C 70.61, H 8.07, N 5.01.

D. Ethyl-7-oxa-9-azabicyclo[3.3.1]nonan-3-carboxylate

Prepared by a procedure analogous to that of Example 9D in 34% yield as an oil, which was used directly in the next step.

E. Ethyl-N-ethoxycarbonylmethyl-7-oxa-9-azabicyclo[3.3.1]nonan-3-carboxylate

Prepared by a procedure analogous to that of Example 9E in 60% yield as an oil.

$^1$H-NMR (δ, CDCl$_3$): 1.14 (overlapping triplets, 6H), 1.65 (m, 2H), 1.97 (m, 2H), 2.72 (broad s, 2H), 3.39 (s, 2H), 3.54 (m, 1H), 3.80 (dd, J=12,55, 4H), 4.03 (overlapping quartets, 2H).

$^{13}$C-NMR (CDCl$_3$): 14.1, 14.2, 25.3, 36.9, 52.3, 53.4, 60.1, 60.5, 71.1, 170.7, 175.5.

IR (KBr, cm$^{-1}$): 1725–1745 (C=O's).

MS (%): 286 (39), 285 (27, parent), 240 (43), 212 (100), 182 (80), 166 (39), 129 (22), 110 (35), 108 (40), 96 (22), 94 (29), 82 (25), 81 (31), 80 7(20), (31), 67 (36), 56 (45), 55 (38), 54 (37), 53 (22).

Anal. Calc'd for C$_{14}$H$_{23}$NO$_5$·1/4H$_2$O: C 58.02, H 8.17, N 4.83, Found: C 57.99, H 8.29, N 5.02.

F. 9-Benzylideno-3-oxa-10-azatricyclo[4.4.1.0$^{5,10}$]undecan-8-one

Prepared by a procedure analogous to that of Example 9F from 3-oxa-10-azabicyclo[4.4.1.0$^{5,10}$]undecan-8-one, which was prepared in 79% yield as an oil and used directly, in 89% yield, mp 124°–125° C.

$^1$H-NMR (δ, CDCl$_3$): 2.12 (m, 4H), 2.58 (m, 1H), 2.98 (m, 2H), 3.85 (dd, J=12,42, 4H), 7.00 (s, 1H), 7.2–7.4 (m, 3H), 8.0–8.1 (m, 2H).

$^{13}$C-NMR (CDCl$_3$): 29.1, 40.6, 50.7, 71.0, 126.1, 128.5, 129.9, 132.2, 133.7, 143.3, 205.8.

IR (KBr, cm$^{-1}$): 1740 (C=O), 1625 (C=C).

MS (%): 255 (100, parent), 227 (61), 226 (95), 198 (58), 197 (92), 196 (81), 155 (67), 129 (51), 128 (64), 117 (61), 116 (73), 91 (58), 89 (64), 77 (60), 55 (61).

G. 9-(Diphenylmethyl)-3-oxa-10-azatricyclo[4.4.1.0$^{5,10}$]undecan-8-one

Prepared by a procedure analogous to that of Example 9G in 36% yield, mp 140°–147° C.

$^1$H-NMR (δ, CDCl$_3$): 1.8–2.1 (m, 4H), 2.29 (m, 1H), 2.42 (m, 1), 2.99 (m, 1H), 3.30 (s, 2H), 3.5–3.7 (m, 3H), 4.70 (d, J=6, 1H), 7.0–7.5 (m, 10H).

$^{13}$C-NMR (CDCl$_3$): 28.3, 29.9, 41.2, 46.6, 48.9, 53.1, 70.8, 71.4, 73.7, 126.5, 128.2, 128.4, 128.7, 128.8, 142.0, 143.4, 219.9.

H. Cis-9-(diphenylmethyl)-N-((2-methoxyphenyl)methyl)-3-oxa-10-azatricyclo[4.4.1.0$^{5,10}$]undecan-8-amine Prepared by a procedure analogous to that of Example 9H in 15% yield, mp 55°–60° C.

$^1$H-NMR (δ, CDCl$_3$): 1.4 (m, 1H), 1.5–1.8 (m, 3H), 2.0–2.2 2H), 2.31 (m, 1H), 2.84 (m, 1H), 3.02 (m, 1H), 3.14 (m, 1H), 3.3–3.5 (m, 3H), 3.67 (dd, J=12, 90, 2H), 3.51 (s, 3H), 4.58 (d, J=12, 1H), 6.6–6.8 (m, 2H), 7.0–7.4 (m, 12H).

$^{13}$C-NMR (CDCl$_3$): 22.3, 25.7, 29.4, 45.3, 46.1, 48.5, 52.3, 54.1, 55.2, 64.4, 71.3, 109.9, 120.1, 125.3, 126.5, 127.8, 127.9, 129.0, 129.4, 143.2, 145.6, 157.5.

IR (KBr, cm$^{-1}$): 1603 (aromatic C=C).

Anal. Calc'd for C$_{30}$H$_{34}$N$_2$O$_2$·1/4H$_2$O: C 78.48, H 7.57, N 6.10. Found: C 78.67, H 7.72, N 5.83.

EXAMPLE 12

2-(Diphenylmethyl)dodecahydro-N-(2-methoxyphenyl)methyl)-2H-1,4-methanobenzo[h]quinolin-3-amine A. Ethyl-3-cyano-5,6-(octahydronaphtho)pyridin-2-one-4-carboxylate Prepared in 46% yield as a mixture of cis and trans isomers at the saturated ring junction, mp 233°–237° C.

$^1$H-NMR (δ, CDCl$_3$): 1.1–2.1 (m, 10H), 1.47 (t, J=7, 3H), 2.37 (m, 1H), 2.5–2.6 (m, 2H), 2.75 (m, 1H), 4.51 (closely overlapping quartets due to the mixture of ring junction isomers, 2H).

IR (cm$^{-1}$, KBr): 2220 (CN), 1740 and 1648 (C=O).

MS (%): 300 (43, parent), 272 (56), 255 (100), 203 (21), 67 (20).

Anal. Calc'd for C$_{17}$H$_{20}$N$_2$O$_3$: C 67.98, H 6.71, N 9.33. Found: C 67.62, H 6.70, N 9.37.

B. Ethyl-5, 6-(octahydronaphtho)pyridin-2-one-4-carboxylate

Prepared in 23% yield as a mixture of isomers (as in part A above).

$^1$H-NMR (δ, CDCl$_3$): 1.0–2.0 (m, 10H), 1.30 (t, J=7, 3H), 2.19 (m, 1H), 2.5–2.7 (m, 3H), 4.27 (q, J=7, 2H), 6.66 (finely split singlet, 1H).

MS (%): 276 (45), 275 (90), 274 (27, parent), 247 (33), 246 (100), 220 (57), 178 (39).

C. Ethyl-5,6-(octahydronaphtho)-2-(1-phenyltetrazol-5-yl)oxy)pyridine-4-carboxylate.

Prepared in 88% yield as a mixture of isomers, mp 85°–98° C.

$^1$H-NMR (δ, CDCl$_3$): 0.8–2.3 (multiplets, 10H), 1.31 (t, J=7, 3H), 2.64 (m, 1H), 2.8–2.9 (m, 2H), 3.0 (m, 1H), 4.30 (q, J=7, 2H), 5.22 (s, 1H), 7.3–7.7 (m, 5H).

$^{13}$C-NMR (CDCl$_3$): 14.2, 21.9, 23.5, 25.1, 25.8, 26.0, 26.47, 26.52, 29.3, 29.5, 29.6, 29.9, 32.8, 33.7, 39.4, 42.6, 47.2, 61.8, 109.2, 109.57, 109.63, 122.4, 129.6, 129.7, 129.8, 129.9, 133.0, 142.17, 142.21, 157.4, 157.6, 160.7, 162.2, 165.4, 165.46, 165.49.

IR (cm$^{-1}$, KBr): 1720 (C=O).

MS (%): 420 (46), 419 (19, parent), 391 (56), 275 (54), 274 (100), 118 (36), 117 (63), 65 (48), 41 (33).

HRMS, Calc'd for C$_{23}$H$_{25}$N$_5$O$_3$: 419.1958. Found: 419.2006.

Anal. Calc'd for C$_{23}$H$_{25}$N$_3$: C 65.86, H 6.01, N 16.70. Found: C 65.58, H 5.97, N 16.76.

D. Ethyl-5,6-(octahydronaphtho)pyridine-4-carboxylate

Prepared in 67% combined yield for the two isomers which were separated by chromatography on silica gel; both products were oils.

$^1$H-NMR (δ, CDCl$_3$): (isomer 1) 1.0–2.0 (m, 10H), 1.34 (t, J=7, 3H), 2.32 (m, 1), 2.78 (m, 1H), 3.0–3.1 (m, 2H), 4.32 (q, J=7, 2H), 7.35 (d, J=4, 1H) 8.44 (d, J=4, 1H); (isomer 2) 1.0–2.0 (m, 10H), 1.30 (t, J=6, 3H), 2.06 (m, 1), 2.9–3.0 (m, 2H), 3.1–3.2 (m, 1H), 4.27 (q, J=6, 2H), 7.32 (d, J=5, 1H), 8.33 (d, J=5, 1 mH).

$^{13}$C-NMR (CDCl$_3$): (isomer 1) 14.2, 26.2, 26.8, 27.1, 29.7, 30.3, 34.0, 39.9, 47.8, 61.3, 19.0.4, 131.3, 137.7, 146.4, 146.5, 161.4, 166.9; (isomer 2) 14.2, 21.6, 233.2, 25.8, 26.5, 29.9, 30.5, 33.1, 43.4, 61.3, 120.47, 120.51, 130.9, 137.7, 146.8, 162.9, 166.8.

IR (cm$^{-1}$, KBr): 1690 (C=O).

MS (%): 259 (62, parent), 230 (68), 204 (100), 186 (38), 176 (31).

E. Ethyl 1-ethoxcarbonlmethyl-1-(1-azatetradecahdrophenanthrene)-4-carboxylate

Prepared in 14.5% yield as a mixture of isomers, as an oil.

$^1$H-NMR ($\delta$, CDCl$_3$): 1.0–2.0 (m, 10H), 1.18 and 1.21 (triplets, 6H), 2.2–2.9 (multiplets, 4H), 3.28 (s, 2H), 4.1 (quartets, 4H)

$^{13}$C-NMR (CDCl$_3$): 14.2, 14.3, 20.5, 21.5, 24.7, 26.6, 29.2, 30.5, 32.2, 36.3, 36.6, 38.2, 49.2, 52.6, 53.5, 60.0, 60.05, 60.1, 60.15, 65.6, 171.0, 175.3)

F. 2-Phenylmethlene)dodecahydro-2H-1,4-methanobenzo[h]quinolin-3-one

Prepared as an oil in 17% yield as a mixture of isomers.

$^1$H-NMR ($\delta$, CDCl$_3$): 0.7–2.2 (m, 17H), 2.37 (finely split doublet, J=2, 1H)) 2.6 (m, 1H), 3.1–3.2 (m, 2H), 6.96 (s, 1H), 7.2–7.3 (m, 3H), 8.0–8.1 (m, 2H).

$^{13}$C-NMR (CDCl$_3$): 19.5, 19.6, 19.9, 20.2, 20.7, 20.9, 25.4, 26.3, 26.5, 26.6, 26.7, 27.5, 28.3, 29.2, 30.0, 30.8, 31.6, 32.4, 32.8, 34.2, 34.5, 35.1, 35.4, 35.9, 36.0, 39.5, 39.7, 40.1, 42.3, 45.3, 45.6, 46.1, 53.0, 59.5, 62.7, 123.9, 128.3, 129.5, 132.2, 134.2, 146.5, 207.0.

IR (cm$^{-1}$, KBr): 1702 (C=O), 1642 (C=C).

MS (%): 321 (56, parent), 293 (88), 202 (55), 172 (73), 159 (74), 157 (100), 135 (48), 130 (44), 95 (63), 91 (69), 81 (62), 79 (56), 77 (47), 67 (90), 55 (57).

HRMS, Calc'd for C$_{22}$H$_{27}$NO: 321.2088. Found: 321.2063.

G. 2-(Diphenylmethyl)dodecahydro-2H-1,4-methanobenzo[h]quinolin-3-one

Prepared in 91% yield as an oily mixture of isomers.

$^1$H-NMR ($\delta$, CDCl$_3$): 0.7–2.0 (m, 17H), 2.05 (m, 1H), 2.19 (m, 1H), 2.49 (m, 1H), 3.12, (m, 1H), 3.86 (d, J=8, 1H), 4.49 (d, J=8, 1H), 7.0–7.4 (m, 10H).

$^{13}$C-NMR (CDCl$_3$): 16.9, 19.4, 20.3, 21.0, 21.1, 26.0, 26.1, 26.3, 26.6, 27.7, 29.0, 30.1, 31.0, 32.0, 32.2, 33.0, 36.2, 40.6, 42.3, 42.8, 44.7, 45.2, 46.3, 47.2, 51.0, 53.4, 60.5, 73.7, 126.1, 126.3, 127.1, 127.8, 128.0, 128.2, 128.4, 128.58, 128.61, 128.7, 128.8, 142.4, 143.8 (carbonyl carbon too faint).

IR (cm$^{-1}$, KBr): 1762 (C=O).

MS (%): 399 (3, parent), 371 (36), 204 (100, 180 (68), 91 (44), 68 (32), 67 (39).

HRMS, Calc'd for C$_{28}$H$_{33}$NO: 399.2556. Found: 399.2532.

H. 2-(Diphenylmethyl)dodecahydro-N-((2-methoxyphenyl)methyl)-2H-1, 4-methanobenzo[h]quinolin-3-amine Prepared in 13% yield as a mixture of isomers, mp 145°–156° C.

$^1$H-NMR ($\delta$, CDCl$_3$): 0.7–2.0 (m, 18H), 2.46 (m, 1H), 2.77 (m, 1H), 2.9–3.0 (m, 2H), 3.53 (dd, J=14, 96, 2H), 3.55 (s, 3H), 3.6–3.7 (m, 1H), 4.60 (d, J=12, 1H), 6.6–7.4 (m, 14H).

$^{13}$C-NMR (CDCl$_3$): 15.3, 20.1, 21.5, 26.1, 26.3, 29.9, 30.0, 30.1, 31.1, 32.1, 32.65, 32.75, 34.6, 36.2, 46.3, 48.7, 48.9, 55.2, 55.6, 55.7, 55.8, 64.5, 65.1, 109.9, 120.1, 125.1, 126.3, 126.4, 127.4, 127.6, 127.9, 128.18, 128.24, 128.3, 128.37, 128.44, 128.8, 129.0, 129.18, 129.26, 129.35, 129.47, 129.51, 143.2, 145.7, 157.4.

IR (cm$^{-1}$, KBr): 1599 (C=C).

MS (%): 399 (34), 354 (36), 353 (98), 344 (36), 218 (42), 204 (39), 135 (51), 122 (41), 121 (100), 92 (86), 91 (89), 81 (50), 79 (50), 77 (34), 70 (46), 69 (43), 68 (37), 67 (70), 65 (32), 56 (36), 55 (50), 77 (34), 70 (46), 69 (43), 68 (37), 67 (70), 65 (32), 56 (36), 55 (55).

HRMS, Calc'd for C$_{36}$H$_{45}$N$_2$O: 521.3528. Found: 521.3493.

Anal. Calc'd for C$_{36}$ $_{H45}$N$_2$O •5/4H$_2$O: C 79.59, H 8.63, N 5.16. Found: C, 79.74, H 8.41, N 4.95

EXAMPLE 13

Cis-8-(diphenylmethyl)-N-(phenylmethyl)-7-azatricyclo[4.4.1.0$^{5,10}$]undecan-9-amine A. N-Benzyl-3-azabicyclo[3.3.1]nonan-9-one To a 2 L round-bottomed flask equipped with condenser and N$_2$ inlet were added 69 mL (0.638 mol) benzylamine and, dropwise, 53 mL concentrated hydrochloric acid. To the mixture obtained on stirring were added 53 mL (0.510 mol) cyclohexanone, 125 mL (0.620 mol) 37% aqueous formaldehyde solution, and 730 mL acetic acid. The solution was heated at 80° C. for 2 hours, then concentrated under reduced pressure. The residue was partitioned between ether and water, and the water layer was washed with ether, the pH adjusted to 8 with solid sodium carbonate, and extracted with methylene chloride. The organic layer was dried over sodium sulfate and evaporated. The residue was taken up in 150 mL ethanol and treated with 50 mL (0.530 mol) acetic anhydride. After stirring for 2 hours, the solution was treated with 53 mL concentrated hydrochloric acid and stirred for an additional 2 hours. It was then concentrated, taken up in water, extracted with methylene chloride, and the pH adjusted to 8 with sodium carbonate. The aqueous layer was then extracted with methylene chloride and the organic layer dried over sodium sulfate and evaporated. The residue was chromatographed on silica gel using hexane/ethyl acetate as eluent to afford 8.84 g (7.6% yield) of the product as a solid, mp 47°–51° C.

$^1$H-NMR ($\delta$, CDCl$_3$): 1.48 (m, 1H), 2.0 (m, 2H), 2.1 (m, 2H), 2.31 (broad s, 2H), 2.51 (m, 2H), 2.94 (m, 1H), 3.13 (m, 2H), 3.43 (s, 2H), 7.2–7.4 (m, 5H)

$^{13}$C-NMR (CDCl$_3$): 21.4, 34.7, 47.8, 60.3, 62.2, 127.1, 128.4, 128.6, 138.6, 218.2.

IR (KBr, cm$^{-1}$): 1720 (C=O).

MS (%): 230 (34), 229 (80, parent), 228 (49), 138 (55), 132 (32), 120 (73), 119 (37), 106 (37), 92 (51), 91 (100), 65 (52), 55 (47).

HRMS, Calc'd for C$_{15}$H$_{19}$NO: 229.1467. Found: 229.1465.

Anal. Calc'd for C$_{15}$H$_{19}$NO: C 78.56, H 8.35, N 6.11. Found: C 78.54, H 8.29, N 6.13.

B. N-Benzyl-3-azabicyclo[3.3.1]nonan-9-carbonitrile

The title compound was prepared by procedure analogous to that of Example 9B in 80% yield as a low melting solid which was a mixture of nitrile stereoisomers.

$^1$H-NMR ($\delta$, CDCl$_3$): 1.2–1.9 (m, 5H), 2.04 (m, 2H), 2.11 (doublets, J=2, 1H), 2.6–2.8 (m, 4H), 2.96 (doublets, J=2, 1H), 3.38 and 3.43 (singlets, 2H), 7.2–7.4 (m, 5H).

$^{13}$C-NMR (CDCl$_3$): 21.18, 21.22, 26.8, 30.9, 31.7, 31.8, 31.9, 34.4, 34.8, 54.9, 58.8, 63.4, 63.5, 121.5, 126.9, 127.0, 128.3, 128.7, 138.5, 138.9.

IR (KBr, cm$^{-1}$): 2218 (CN).

MS (%): 240 (48, parent), 239 (43), 163 (35), 149 (66), 120 (33), 91 (100), 65 (38).

Anal. Calc'd for C$_{16}$H$_{20}$N$_2$: C 79.96, H 8.39, N 11.66. Found: C 79.87, H 8.27, N 11.50.

C. Ethyl-N-benzyl-3-azabicylo[3.3.1]nonan-9-carboxylate

The title compound was prepared in 33% yield as an oily mixture of stereoisomers using a analogous procedure to that of Example 9C.

$^1$H-NMR ($\delta$, CDCl$_3$): 1.26 (overlapping triplets, 3H), 1.3–1.9 (m, 5H), 2.2–2.4 (m, 5H), 2.6–2.8 (m, 2H), 2.92 (m, 1H), 3.33 and 3.40 (singlets, 2H), 4.17 (overlapping quartets, 2H), 7.1–7.3 (m, 5H).

IR (KBr, cm$^{-1}$): 1730 (C=O).

MS (%): 287 (26, parent), 196 (82), 134 (30), 91, (100).

HRMS Calc'd for $C_{18}H_{25}NO_2$: 287.1883. Found: 287.1872.

D. Ethyl-3-azabicyclo[3.3.1]nonan-9-carboxylate

The title compound was prepared as an oil using a procedure analogous to that Example of 9D, and was used directly in the next step.

E. Ethyl-N-ethoxycarbonylmethyl-3-azabicyclo[3.3.1]nonan-9-carboxylate

The title compound was prepared using a procedure analogous to that of Example 9E.

$^1$H-NMR ($\delta$, CDCl$_3$): 1.1 (overlapping triplets, 6H), 1.4–1.8 (m, 5H), 2.0–2.2 (m, 3H), 2.4–2.6 (m, 4H), 2.82 (m, 1H), 2.88 and 2.98 (singlets, 2H), 4.0 (overlapping quartets, 2H).

$^{13}$C-NMR (CDCl$_3$): 14.1, 20.8, 21.0, 26.7, 30.6, 30.8, 32.4, 45.6, 46.1, 54.7, 59.2, 59.6, 59.7, 59.8, 59.9, 60.0, 60.1, 170.7, 170.8, 173.4, 173.5.

IR (KBr, cm$^{-1}$): 1735 (C=O).

MS (%): 283 (7, parent), 211 (33), 210 (100) 95 (17), 93 (17), 58 (46).

HRMS Calc'd for $C_{15}H_{25}NO_4$: 283. 1785. Found: 283. 1764.

F. 7-Azatricyclo[4.4.1.0$^{5,10}$]undecan-9-one

The title compound was prepared in 83% yield as an oil using a procedure analogous to that of Example 3F and used directly in the next step.

G. 8-Benzylidene-7-azatricyclo[4.4.1$^{5,10}$]undecan-9-one

The title compound was prepared using a procedure analogous to that of Example 3F in 75% yield, mp 133°–137° C.

$^1$H-NMR ($\delta$, CDCl$_3$): 1.3–1.6 (m, 5H), 1.9–2.0 (m, 1H), 2.25 (m, 1H), 2.34 (m, 1H), 2.8–3.1 (m, 4H), 6.99 (2, 1H), 7.2–7.4 (m, 3H), 7.99 (m, 2H).

$^{13}$C-NMR (CDCl$_3$): 14.2, 27.8, 29.0, 49.0, 51.9, 124.9, 128.4, 129.5, 132.1, 134.0, 144.4, 206.1.

IR (KBr, cm$^{-1}$): 1700 (C=O), 1621 (C=C).

MS (%): 254 (32), 253 (100 parent), 225 (76), 224 (94), 130 (30), 77 (43), 67 (41).

Anal. Calc'd for $C_{17}H_{19}NO$: C 80.60, H 7.56, N 5.53. Found: C 80.57, H 7.67, N 5.49.

H. 8-(Diphenylmethyl)-7-azatricyclo[4.4.1.0$^{5,10}$]undecan-9-one

The title compound was prepared in 72% yield as an oil using a procedure analogous to that of Example 3G.

$^1$H-NMR ($\delta$, CDCl$_3$): 1.2–1.6 (m, 4H), 1.82 (m, 1H), 2.12 (m, 1H), 2.20 (m, 1H), 2.28 (m, 1H), 2.37 (dd, J=4, 14, 1H), 2.70 (m, 1H), 2.92 (dd, J=4, 16, 1H), 3.15 (m, 1H), 3.85 (d, J=8, 1H), 4.53 (d, J=8, 1H), 7.1–7.5 (m, 10H).

$^{13}$C-NMR (CDCl$_3$): 14.3, 27.6, 27.7, 28.8, 30.0, 46.1, 49.6, 50.3, 54.6, 71.5, 126.5, 126.6, 128.4, 128.5, 142.3, 143.3, 219.4.

IR (KBr, cm$^{-1}$): 1710 (C=O).

MS (%): 331 (2, parent), 304 (48), 303 (100) 302 (39), 223 (38), 222 (100), 180 (75), 179 (35), 167 (52), 165 (57), 136 (71), 91 (74).

Anal. Calc'd for $C_{23}H_{25}NO$: C 83.35, H 7.60, N 4.23. Found: C 83.89, H 7.71, N 4.27.

I. Cis-8-(diphenylmethyl)-N-(phenylmethyl)-7-azatricyclo[4.4.1.0$^{5,10}$]undecan-9-amine The title compound was prepared using a procedure analogous to that of Example 3H as the hydrochloride salt in 28% yield, mp 218°–222° C.

$^1$H-NMR ($\delta$, CDCl$_3$): (free base) 1.3–1.9 (m, 9H), 2.2–2.4 (m, 2H), 2.76 (m, 2H), 2.92 (dd, J=4, 10, 1H), 3.38 (dd, J=12, 102, 2H), 3.64 (dd, J=9, 12, 1H), 4.46 (d, J=12, 1H), 6.64 (m, 2H), 7.0–7.4 (m, 13H).

$^{13}$C-NMR (CDCl$_3$): 15.4, 15.8, 23.3, 29.3, 29.7, 29.9, 34.2, 36.4, 45.7, 49.7, 52.0, 55.2, 55.6, 62.6, 65.9, 126.0, 126.5, 126.6, 126.7, 127.5, 127.8, 127.9, 128.0, 128.2, 128.4, 129.3, 139.9, 143.8, 145.4.

IR (KBr, cm$^{-1}$): 1561 (C=C).

MS (%): 422 (<1, parent), 331 (24), 256 (29) 255 (100), 136 (922), 90 (68).

Anal. Calc'd for $C_{30}H_{34}N_2 \cdot 2HCl \cdot 9/4H_2O$: C 67.22, H 7.61, N 5.23. Found: C 67.00, H 7.42, N 5.13.

EXAMPLE 14

Cis-8-(diphenylmethyl)-N-((2-methoxyphenyl)methyl)-7-azatricyclo[4.4.1.0$^{5,10}$]undecan-9-amine The title compound was prepared in 36% yield using a procedure analogous to that of Example 3H, mp 97°–102° C.

$^1$H-NMR ($\delta$, CDCl$_3$): 1.3–1.8 (m, 8H), 2.30 (m, 2H), 2.55 (m, 2H), 2.93 (dd, J=3, 10, 1H), 3.24 (m, 1H), 3.44 (dd, J=13, 84, 2H), 3.54 (s, 3H), 3.65 (dd, J=8, 12, 1H), 4.53 (d, J=12, 1H), 6.6–6.8 (m, 3H), 7.0–7.4 (m, 11H).

$^{13}$C-NMR (CDCl$_3$): 15.8, 23.1, 29.3, 29.7, 29.9, 34.1, 45.6, 45.9, 49.5, 55.0, 55.1, 55.2, 62.6, 109.9, 120.1, 126.0, 126.4, 127.6, 127.7, 127.8, 127.9, 128.4, 129.1, 129.3, 143.6, 145.6, 157.4.

IR (KBr, cm$^{-1}$): 1600 (C=C).

MS (%): 452 (3, parent), 331 (52), 285 (100) 136 (38), 121 (54), 91 (51).

Anal. Calc'd for $C_{31}H_{36}N_2O \cdot 1/2H_2O$: C 80.66, H 8.08, N 6.07. Found: C 80.43, H 7.89, N 5.89.

EXAMPLE 15

Cis-8-(diphenylmethyl)-N-((2-chlorophenyl)methyl)-7-azatricyclo[4.4.1.0$^{5,10}$]undecan-9-amine The title compound was prepared using a procedure analogous to that of Example 3H in 67% yield, mp 115°–118° C.

$^1$H-NMR ($\delta$, CDCl$_3$): 1.3–1.6 (m, 5H), 1.7–1.9 (m, 3H), 2.29 (m, 2H), 2.76 (m, 2H), 2.93 (dd, J=3, 10, 1H), 3.12 (m, 1H), 3.34 (m, 1H), 3.6–3.8 (m, 2H), 4.48 (d, J=12, 1H), 6.63 (m, 1H), 7.0–7.4 (m, 13H).

$^{13}$C-NMR (CDCl$_3$): 15.8, 23.3, 29.5, 29.7, 29.9, 34.5, 45.6, 48.9, 55.2, 55.6, 62.6, 126.0, 126.5, 127.5, 128.0, 128.4, 129.2, 129.8, 133.8, 137.5, 143.7, 145.5.

IR (cm$^{-1}$): 1599 and 1571 (C=C).

MS (%): 456 (<1, parent Cl$^{35}$), 331 (31), 291 (33) 289 (100), 136 (949), 127 (32), 125 (86), 91 (63).

Anal. Calc'd for $C_{30}H_{33}N_2Cl$: C 78.84, H 7.28, N 6.13. Found: C 78.58, H 7.19, N 6.05.

EXAMPLE 16

Cis-8-(diphenylmethyl)-N-((4-trifluoromethylphenyl)methyl)-7-azatricyclo[4.4.1.0$^{5,10}$]undecan-9-amine The title compound was prepared in 40% yield using a procedure analogous to that of Example 3H, mp 131°–135° C.

$^1$H-NMR ($\delta$, CDCl$_3$): 1.3–2.1 (m, 8H), 2.24 (m, 1H), 2.34 (dd, J=2, 14, 1H), 2.76 (m, 2H), 2.91 (dd, J=2, 10, 1H), 3.24 (m, 1H), 3.41 (dd, J=13, 102, 2H), 3.73 (dd, J=8, 12, 1H), 4.43 (d, J=12, 1H), 6.74 (In, 2H), 7.1–7.5 (m, 12H).

$^{13}$C-NMR (CDCl$_3$): 15.7, 23.2, 29.1, 29.5, 29.8, 34.2, 45.6, 49.7, 51.4, 55.1, 55.5, 62.6, 125.1, 126.2, 126.6, 127.5, 128.0, 128.6, 128.7, 129.4, 143.6, 144.0, 144.8.

IR (KBr, cm$^{-1}$): 1620, 1600 (C=C).

MS (%): 490 (<2, parent), 332 (24), 331 (66), 324 (37), 323 (100), 180 (22), 159 (53), 136 (21).

Anal. Calc'd for $C_{31}H_{33}N_2F_3$: C 75.89, H 6.78, N 5.71. Found: C 75.75, H 6.69, N 5.58.

EXAMPLE 17

Cis-8-diphenylmethyl-N-((2-methoxyphenyl)methyl)-7-azatricyclo[4.3.1.0$^{4,9}$]decan-9-amine A. N-Benzyl-3-azabicyclo[3.2.1]octan-8-one The title compound was prepared as an oil in 4% yield using a procedure analogous to that of Example 13A.

$^1$H-NMR (δ, CDCl$_3$): 1.82 (m, 2H), 2.04 (m, 2H), 2.13 (m, 2H), 2.51 (d, J=12, 2H), 2.94 (dd, J=3, 12, 2H), 3.57 (s, 2H), 7.2–7.4 (m, 5H).

$^{13}$C-NMR (δCDCl$_3$): 22.8, 45.4, 60.2, 61.7, 127.2., 128.3, 128.6, 138.8, 220.1.

MS (%): 215 (30, parent), 124 (17), 91 (100), 65 (14), 55 (16), 42 (15), 41 (17).

HRMS, Calc'd for $C_{14}H_{17}NO$: 215.1254. Found: 215.1316.

B. N-Benzyl-3-azabicyclo[3.2.1]octan-8-carbonitrile

The title compound was prepared as an oil in 99% yield using a procedure analogous to that of Example 9B.

$^1$H-NMR (δ, CDCl$_3$): 1.63 (m, 1H), 1.8–2.0 (m, 3H), 2.05 (d, J=11, 1H), 2.35 (m, 1H), 2.4–2.8 (m, 3H), 2.71 (dd, J=3, 11, 1H), 3.46 and 3.53 (singlets, 2H), 7.2–7.4 (m, 5H).

IR (cm$^{-1}$, neat): 2220 (CN).

MS (%): 226 (41, parent), 225 (31), 149 (37), 135 (59), 91 (100), 65 (34).

C. Ethyl-N-Benzyl-3-azabicyclo[3.2.1]octan-8-carbonitrile

The title compound was prepared using a procedure analogous to that of Example 9C in quantitative yield as an oily mixture of isomers at the 8-position:

$^1$H-NMR (δ, CDCl$_3$): 1.25 (triplets, 3H), 1.6–1.8 (m, 4H), 2.02 (s, 1H), 2.10 (d, J=8.5, 2H), 2.3–2.5 (m, 4H), 2.72 (dd, J=4, 11, 2H), 3.43 and 3.48 (singlets, 2H), 4.17 (quartet, 2H), 7.1–7.4 (m, 5H).

$^{13}$C-NMR (δ, CDCl$_3$): 14.2, 14.4, 27.4, 28.5, 36.7, 38.3, 49/4, 54.4, 55.2, 59.8, 60.1, 61.9, 62.3, 126.7, 126.8, 128.1, 128.6, 139.3, 139.5, 172.7, 174.0.

IR (cm$^{-1}$, neat): 1740 (C=O).

MS (%): 273 (62, parent), 272 (43), 200 (37), 182 (91), 134 (62), 92 (31), 91 (100).

D. Ethyl-N-ethoxycarbonylmethyl-3-azabicyclo[3.2.1]octan-8-carboxylate

The title compound was prepared by a procedure analogous to that of Example 9E in 75% overall yield as an oily mixture of isomers at the 8-position:

$^1$H-NMR (δ, CDCl$_3$): 1.10 (triplets, 6H), 1.5–1.7 (m, 4H), 2.19 (s, 1H), 2.3–2.5 (m, 4H), 2.6 (m, 2H), 3.00 and 3.09 (singlets, 2H), 4.0 (quartets, 4H).

$^{13}$C-NMR (δ, CDCl$_3$): 14.08, 14.15, 14.19, 27.0, 28.1, 36.3, 38.0, 48.6, 53.6, 54.5, 58.1, 58.7, 59.1, 59.7, 60.0, 170.6, 172.3, 173.7.

IR (cm$^{-1}$, neat): 1737 (C=O).

MS (%): 269 (15, parent), 196 (100), 81 (34), 79 (36), 58 (55), 57 (37)

Anal. Calc'd for $C_{14}H_{23}NO_4 \bullet 1/4H_2O$: C 61.41, H 8.65, N 5.11. Found: C 61.53, H 8.69, N 5.07.

E. 7-Azatricyclo[4.3.1.0$^{4,9}$]decan-9-one

The title compound was prepared as an intemediate by a procedure analogous to that of Example 13F in 74% yield, and used without further characterization.

F. 8-Benzylidene-7-azatricyclo[4.3.1.0$^{4,9}$]decan-9-one

The title compound was prepared by a procedure analogous to that of Example 3F in 87% yield, mp 134°–140° C.

$^1$H-NMR (δ, CDCl$_3$): 1.67 (m, 2H), 1.95 (m, 2H), 2.42 (m, 1H), 2.49 (m, 2H), 2.69 (m, 2H), 3.17 (m, 2H), 6.93 (s, 1H), 7.2–7.4 (m, 3H), 7.98 (m, 2H).

$^{13}$C-NMR (δ, CDCl$_3$): 32.8, 38.9, 52.3, 58.5, 123.1, 128.4, 129.5, 132.3, 133.9, 144.3, 205.6.

IR (cm$^{-1}$, KBr): 1700 (C=O), 1630 (C=C).

MS (%): 239 (100, parent), 211 (75), 210 (96), 182 (32), 156 (30), 130 (33), 116 (31), 77 (33).

Anal. Calc'd for $C_{16}H_{17}NO$: C 80.30, H 7.16, N 5.85. Found: C 80.36, H 6.91, N 5.58.

G. 8-Diphenylmethyl-7-azatricyclo[4.3.1.0$^{4,9}$]decan-9-one

The title compound was prepared as an oil in 38% yield by a procedure analogous to that of Example 3G.

$^1$H-NMR (δ, CDCl$_3$): 1.55 (m, 1H), 1.65 (m, 1H), 1.89 (m, 2H), 2.11 (m, 1H), 2.25 (m, 1H), 2.43 (m, 1H), 2.51 (m, 1H), 2.65 (m, 1H), 2.92 (m, 1H), 3.30 (m, 1H), 3.81 (d, J=8, 1H), 4.50 (d, J=8, 1H), 7.1–7.5 (m, 10H).

$^{13}$C-NMR (δ, CDCl$_3$): 32.7, 38.5, 40.2, 50.3, 52.3, 52.6, 60.8, 71.2, 126.47, 126.52, 128.4, 128.5, 128.6, 142.2, 143.2, 219.3.

IR (cm$^{-1}$, neat): 1715 (C=O).

MS (%): 317 (6, parent), 289 (96), 222 (100), 213 (56), 184 (54), 180 (53), 167 (50), 165 (55), 152 (59), 122 (62), 91 (91), 79 (55), 67 (53), 55 (52).

Anal. Calc'd for $C_{22}H_{23}NO$: 317.1812. Found: 317. 1764.

H. Cis-8-diphenylmethyl-N-((2-methoxyphenyl)methyl)-7-azatricyclo[4.3.1.0$^{4,9}$]decan-9-amine The title compound was prepared in 33% yield by. a procedure analogous to that of Example 3H, mp 147°–151° C.

$^1$H-NMR (δ, CDCl$_3$): 1.3–1.6 (m, 2H), 1.6–1.8 (m, 2H), 2.02 (m, 3H), 2.1–2.4 (m, 3H), 2.98 (m, 1H), 3.13 (m, 1H), 3.5 (dd, 2H), 3.57 (s, 3H), 3.6 (m, 1H), 4.52 (d, J=12, 1H), 6.6–6.8 and 7.1–7.4 (m, 14H).

$^{13}$C-NMR (δ, CDCl$_3$): 30.7, 31.5, 32.7, 34.5, 38.6, 46.4, 49.4, 49.6, 53.0, 55.2, 60.4, 62.8, 110.0, 120.1, 125.8 126.3, 127.7, 128.2, 128.3, 129.0, 129.4, 143.5, 145.5, 145.7, 157.4.

IR (cm$^{-1}$, KBr): 1602 (C=C).

MS (%): 438 (1, parent), 317 (46), 272 (30), 271 (100), 121 (62), 91 (61).

Anal. Calc'd for $C_{30}H_{34}N_2O \bullet 1/2H_2O$: C 80.50, H 7.88, N 6.26. Found C 80.86, H 7.77, N 6.18.

I claim:

1. A compound of the formula

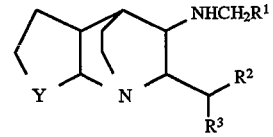

wherein Y is $(CH_2)_m$ wherein m is an integer from one to three

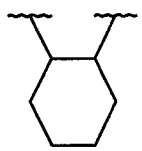

$R_3$ is thienyl, phenyl, fluorophenyl, chlorophenyl or bromophenyl;

$R^1$ is cycloalkyl having from five to seven carbon atoms, pyrrolyl, thienyl, pyridyl, phenyl or substituted phenyl, wherein said substituted phenyl is substituted with one to three substituents selected from fluorine, chlorine, bromine, trifluoromethyl, alkyl having from one to three carbon atoms, alkoxy having from one to three carbon atoms, carboxy, alkoxycarbonyl having from one to three carbons in the alkoxy moiety and benzyloxycarbonyl; and $R^2$ is furyl, thienyl, pyridyl, indolyl, biphenyl, phenyl or substituted phenyl, wherein said substituted phenyl is substituted with one or two substituents selected from fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzyloxycarbonyl, or a pharmaceutically acceptable salt thereof.

2. A compound as claimed in claim 1 wherein Ar, $R^1$ and $R^2$ are each phenyl.

3. A compound as claimed in claim 1 wherein $R_3$ is phenyl, $R^1$ is 2-chlorophenyl and $R^2$ is phenyl.

4. A compound as claimed in claim 1 wherein $R_3$ is phenyl, $R^1$ is 2-trifluoromethylphenyl and $R^2$ is phenyl.

5. A compound as claimed in claim 1 wherein $R_3$ is phenyl, $R^1$ is 2-methoxyphenyl and $R^2$ is phenyl.

6. A compound as claimed in claim 1 wherein Ar, $R^1$ and $R^2$ are each phenyl.

7. A compound as claimed in claim 1 wherein $R_3$ is phenyl, $R^1$ is 2-chlorophenyl and $R^2$ is phenyl.

8. A compound as claimed in claim 1 wherein $R_3$ is phenyl, $R^1$ is 2-trifluromethylphenyl and $R^2$ is phenyl.

9. A compound as claimed in claim 1 wherein $R_3$ is phenyl, $R^1$ is 2-methoxyphenyl and $R^2$ is phenyl.

10. A compound as claimed in claim 1 wherein Ar, $R^1$ and $R^2$ are each phenyl.

11. A compound as claimed in claim 1 wherein $R_3$ is phenyl, $R^1$ is 2-chlorophenyl and $R^2$ is phenyl.

12. A compound as claimed in claim 1 wherein $R_3$ is phenyl, $R^1$ is 4-trifluoromethylphenyl and $R^2$ is phenyl.

13. A compound as claimed in claim 1 wherein $R_3$ is phenyl, $R^1$ is 2-methoxyphenyl and $R^2$ is phenyl.

14. A pharmaceutical composition useful for treating a condition selected from gastrointestinal disorders, central nervous system disorders, inflammatory diseases, pain and migraine in a mammal, comprising an amount of a compound as claimed in claim 1 effective in antagonizing the effect of substance P at its receptor site and a pharmaceutically acceptable carrier.

15. A method of treating a condition selected from gastrointestinal disorders, central nervous system disorders, inflammatory diseases, pain and migraine in a mammal, comprising administering to a mammal in need of such treatment an amount of a compound as claimed in claim 1 effective in antagonizing the effect of substance P at its receptor site.

16. A method for treating a disease or condition medicated by an excess of substance p in a mammal, comprising administering to a mammal in need of such treatment a compound as claimed in claim 1 in an amount that is effective in antagonizing the effects of substance P at its receptor site.

17. A compound as claimed in claim 1, where said compound is selected from:

cis-(1,4-ethano)-3-(phenylmethylamino)-2-benzhydryldecahydroquinoline;

cis-(1,4-ethano)-3-((2-methoxyphenyl)methylamino)-2-benzhydryldecahydroquinoline;

5,6-trimethylene-3-((2-methoxyphenyl)methylamino)-2-benzhydryl-quinuclidine;

5,6-trimethylene-3-benzylamino-2-benzhydryl-quinuclidine; 2-(diphenylmethyl)dodecahydro-N-(2-methoxyphenyl)methyl)-2H-1,4-methanobenzo[h]quinolin-3-amine.

* * * * *